United States Patent
Wu

(10) Patent No.: US 11,065,244 B2
(45) Date of Patent: Jul. 20, 2021

(54) METHODS OF USE OF TETRAHYDROBERBERINE (THB)

(71) Applicant: DIGNITY HEALTH, San Francisco, CA (US)

(72) Inventor: Jie Wu, Avondale, AZ (US)

(73) Assignee: Dignity Health, Phoenix, AZ (US)

( * ) Notice: Subject to any disclaimer, the term of this patent is extended or adjusted under 35 U.S.C. 154(b) by 0 days.

(21) Appl. No.: 16/445,492

(22) Filed: Jun. 19, 2019

(65) Prior Publication Data

US 2019/0328724 A1 Oct. 31, 2019

Related U.S. Application Data

(63) Continuation-in-part of application No. 15/832,414, filed on Dec. 5, 2017, now abandoned, which is a continuation of application No. 13/695,407, filed as application No. PCT/US2011/034834 on May 2, 2011, now abandoned.

(60) Provisional application No. 61/330,589, filed on May 3, 2010.

(51) Int. Cl.
*A61K 31/4738* (2006.01)

(52) U.S. Cl.
CPC ................. *A61K 31/4738* (2013.01)

(58) Field of Classification Search
CPC .... A61K 31/4375; A61K 31/4745; A61P 3/10
See application file for complete search history.

(56) References Cited

U.S. PATENT DOCUMENTS

2007/0231273 A1* 10/2007 Wu .................... A61K 31/4745
424/48
2013/0045987 A1* 2/2013 Wu .......................... A61P 3/10
514/280

FOREIGN PATENT DOCUMENTS

KR    10-2005-0082447    *  8/2005    ......... A61K 31/4375
KR       20050082447 A  *  8/2005

OTHER PUBLICATIONS

Reagan-Shaw et al, FASEBJ vol. 22 pp. 659-661. Published 2007. (Year: 2007).*
Jackson Labs: How much blood can I take from a mouse without endangering its health (Year: 2005).*
Definition of "amount". English Oxford Dictionary. Published 2018 (Year: 2018).*

* cited by examiner

*Primary Examiner* — Theodore R. Howell
*Assistant Examiner* — George W Kosturko

(57) ABSTRACT

Tetrahydroberberine (THB), isolated from the Chinese herb "*Corydalis ambigua*", exhibits a variety of pharmacological effects, although mechanisms of action are unclear or entirely unknown. Described herein are novel methods of using tetrahydroberberine (THB), THB analogs or derivatives, tetrahydroprotoberberines (THPB). Tetrahydroberberine (THB) and analogs such as l-stepholidine (l-SPD) potently block functional $K_{ATP}$ channels natively expressed on midbrain dopamine neurons. Further, THB also blocks pancreatic β-cell $K_{ATP}$ channels, and can be developed to a novel drugs for treating disease and/or conditions such as diabetes and Parkinson's disease.

14 Claims, 13 Drawing Sheets

Figure 1.
A. Tetrahydroberberine (THB)
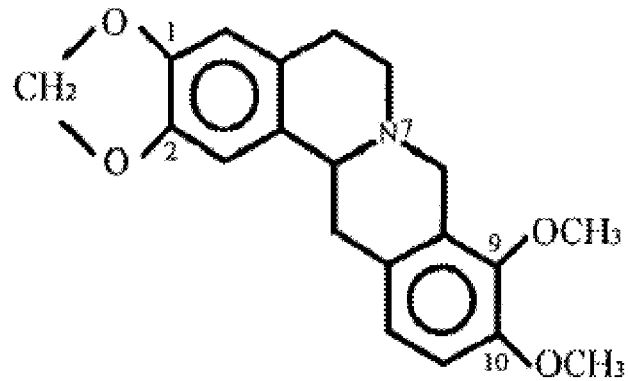
B. *l*-Tetrahydropalmatine (*l*-THP)
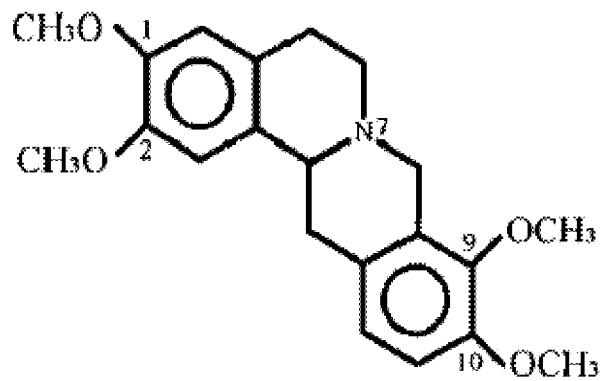
C. *l*-Stepholidine (*l*-SPD)
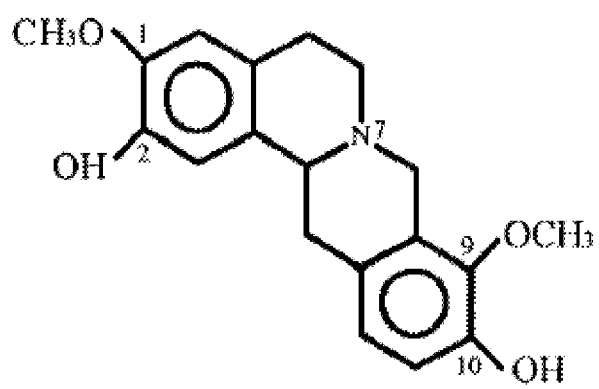

Figure 3.
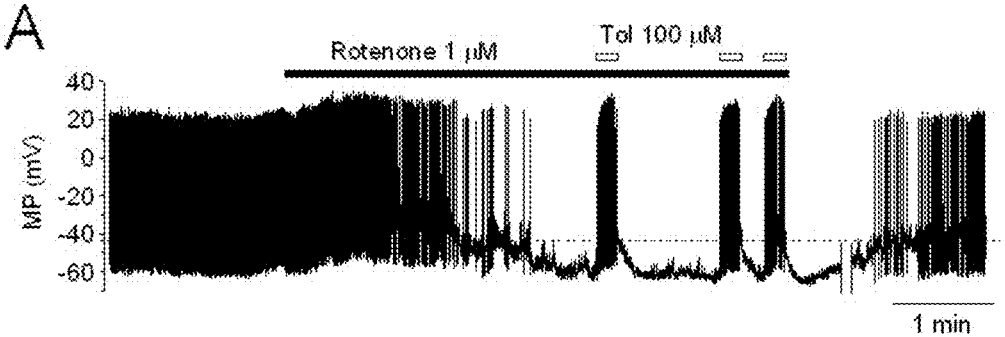
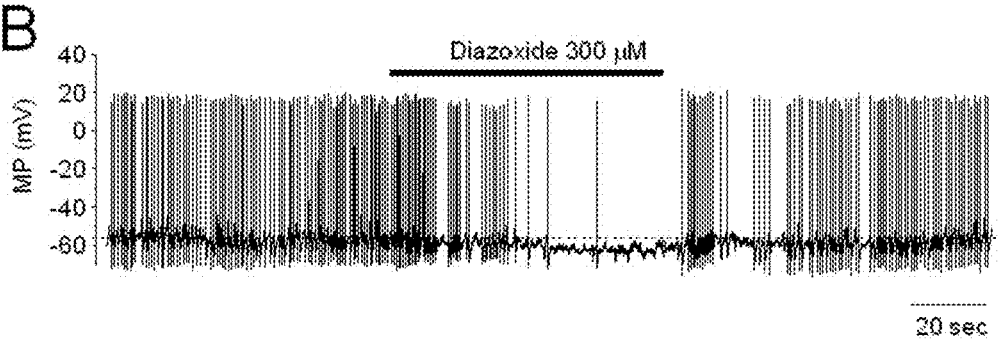
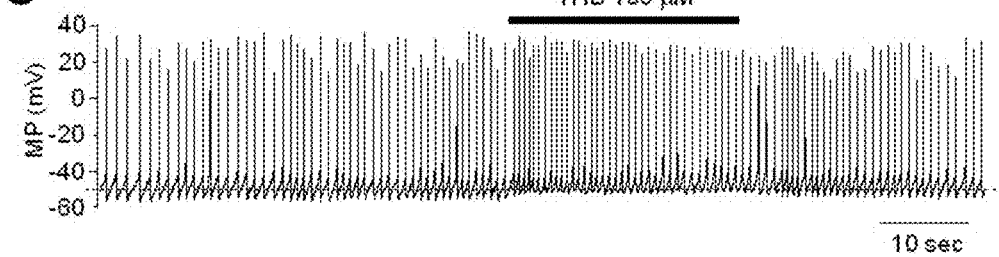
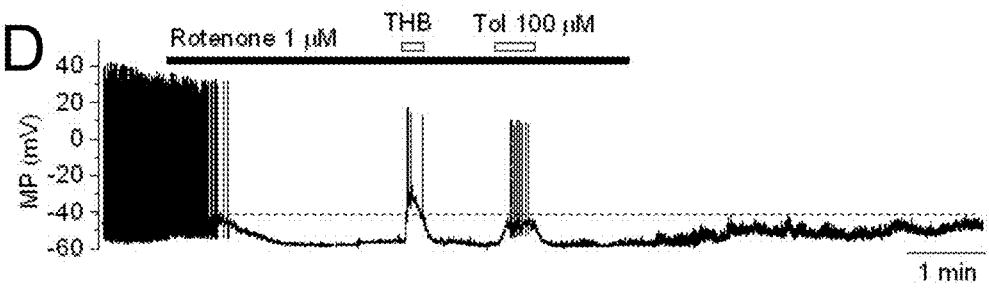

Figure 8.
A Kir6.2/SUR1 (cell-attached)
Control
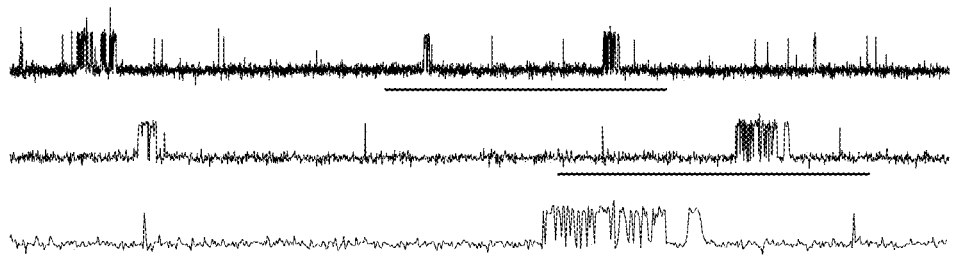
Tetrahydroberberine (100 μM)
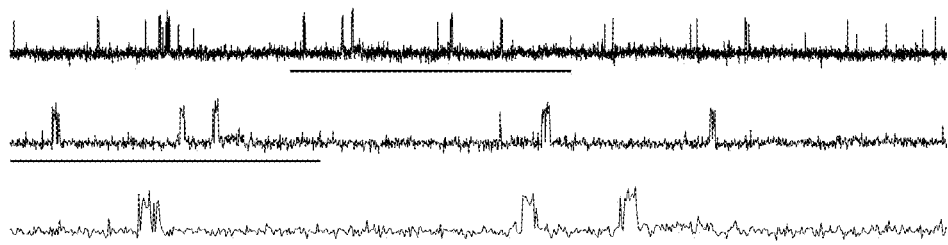
B
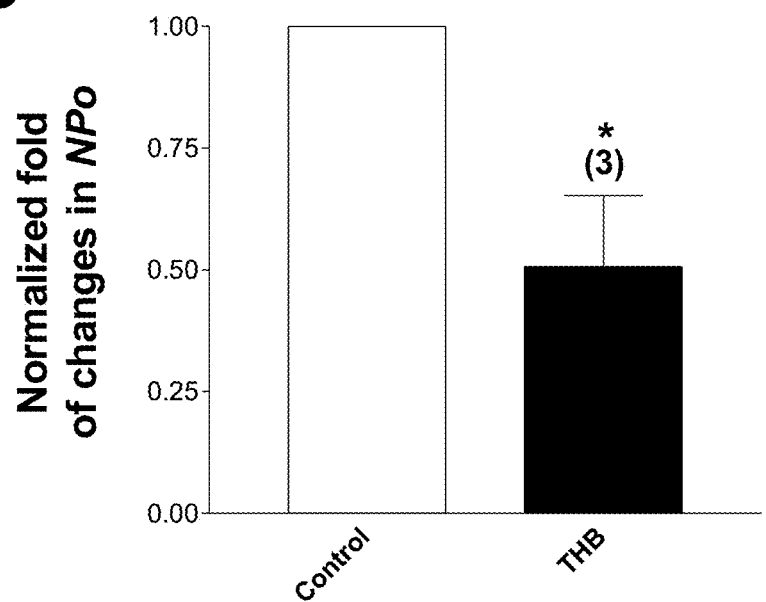

METHODS OF USE OF TETRAHYDROBERBERINE (THB)

CROSS-REFERENCE TO RELATED APPLICATIONS

This application is a continuation-in-part of U.S. patent application Ser. No. 15/832,414, filed Dec. 5, 2017, which was a continuation application of U.S. patent application Ser. No. 13/695,407, filed Oct. 30, 2012, now abandoned, which was a National Phase of International Application No. PCT/US2011/034834, filed May 2, 2011, which further claimed priority to U.S. Provisional Patent Application Ser. No. 61/330,589, filed May 3, 2010. All of these references are hereby incorporated by reference in their entireties for any reasons and uses.

FIELD OF THE INVENTION

This invention relates to novel methods of using tetrahydroberberine (THB), THB pharmaceutical equivalents, salts, analogs or derivatives thereof, and tetrahydroprotoberberines (THPB) for modulating signaling in various diseases and/or conditions.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

Tetrahydroberberine (THB), isolated from the Chinese herb "*Corydalis ambigua*", exhibits a variety of pharmacological effects on the central nervous system (CNS). Molecules such as l-tetrahydropalmatine (l-THP) and l-stepholidine (l-SPD) are analogs of THB. and members of the tetrahydroprotoberberine (THPB) family of molecules. Accumulating lines of evidence indicate that THPB family of molecules exhibit the effects of sedation, hypnosis, antinociception, anti-schizophrenia, antihypertension, and the prevention of drug addiction[1, 4, 33, 39]. In addition, the morphological and biochemical experiments have demonstrated that THPBs also have neuroprotective effects [25]. However, the targets and underlying mechanisms of THPB-induced neuroprotection still remain elusive.

Although extensive works have indicated that DA receptors (D1 and D2) are targets that mediate pharmacological effects of THPBs [2, 3, 5, 7, 9, 10, 22, 23, 25, 37, 38, 40], other targets also have been reported to mediate THPBs' effects including α-adrenergic receptor [16], serotonin 5-HT receptor [17], Ca2+ channels [14, 17, 21] and K+ channels [30-32]. These lines of evidence suggest that THPBs may act on multiple targets to exert their pharmacological effects on the CNS, including brain neurons, by interacting with receptors and channels present in these tissues. Further emerging evidence indicates that ATP-sensitive potassium ($K_{ATP}$) channels in the midbrain substantia nigra compacta (SNc) DA neurons promote pathogenesis in Parkinson disease (PD) animal models.

In addition to various brain neurons, $K_{ATP}$ channels are also widely expressed in a variety of tissues including cardiovascular cells, muscle cells, and pancreatic β-cells. In pancreatic β-cells, $K_{ATP}$ channels play a critical role in the regulation of β-cell excitation and insulin secretion. Diabetes is a group of diseases characterized by high levels of blood glucose resulting from defects in insulin production, insulin action, or both. The closing of $K_{ATP}$ channels causes β-cell depolarization, which in turn activates voltage-sensitive Ca2+ channels and increases cytosolic Ca2+ concentrations, thereby leading to insulin secretion. Therefore, many $K_{ATP}$ channel closers have been used for many years for the treatment of type-2 diabetes.

SUMMARY OF THE INVENTION

The following embodiments and aspects thereof are described and illustrated in conjunction with compositions and methods which are meant to be exemplary and illustrative, not limiting in scope. The present invention provides a method of treating a disease and/or condition associated with $K_{ATP}$ channel signaling in an individual, comprising providing a quantity of a composition comprising tetrahydroberberine (THB), or a pharmaceutical equivalent, analog, derivative, or salt thereof, and treating the individual by administering a therapeutically effective amount of the composition comprising tetrahydroberberine (THB), or a pharmaceutical equivalent, analog, derivative, or salt thereof to the individual. In another embodiment, the tetrahydroberberine (THB), or a pharmaceutical equivalent, analog, derivative, or salt thereof is a tetrahydroprotoberberine (THPB). In another embodiment, the tetrahydroprotoberberine (THPB) is l-stepholidine (l-SPD), and/or l-tetrahydropalmatine (l-THP). In another embodiment, the $K_{ATP}$ channel signaling is part of a dopaminergic receptor, an adrenergic receptor, and/or a serotonin receptor. In another embodiment, the dopaminergic receptor is a D1, D2, D3, D4, or D4 receptor subtype. In another embodiment, the $K_{ATP}$ channel is a Kir 6.1 and/or Kir 6.2 subtype. In another embodiment, the $K_{ATP}$ channel is a SUR1, SUR2A, and/or SUR2B subtype. In another embodiment, the disease and/or condition is a neurodegenerative disease. In particular embodiment, the neurodegenerative disease and/or condition is Parkinson's disease. In particular embodiment, the disease and/or condition is diabetes. In another embodiment, the therapeutically effective amount is between 20 and 150 μM THB. In another embodiment, the therapeutically effective amount is between 100 and 300 μM THB. In another embodiment, the tetrahydroberberine (THB), or a pharmaceutical equivalent, derivative, analog, and/or salt thereof inhibits $K_{ATP}$ channel signaling. In another embodiment, the individual is a human. In another embodiment, the individual is a rat and/or mouse. In a particular embodiment, the $K_{ATP}$ channel signaling is in a neuron. In a particular embodiment, the $K_{ATP}$ channel signaling is in a pancreatic β-cell. In another embodiment, the composition further comprises tolbutamide. In another embodiment, the composition is administered intravenously, orally, topically, and/or through direct injection.

The present invention provides a method of modulating a $K_{ATP}$ channel in a cell, comprising, providing a quantity of a composition comprising tetrahydroberberine (THB), or a pharmaceutical equivalent, derivative, analog, and/or salt thereof, and administering an effective dosage of the composition comprising tetrahydroberberine (THB), or a pharmaceutical equivalent, derivative, analog, and/or salt thereof to the cell. In another embodiment, the tetrahydroberberine (THB), or pharmaceutical equivalent, derivative, analog, and/or salt thereof, inhibits the $K_{ATP}$ channel. In another embodiment, the tetrahydroberberine (THB), or a pharmaceutical equivalent, analog, derivative, or salt thereof is a tetrahydroprotoberberine (THPB). In another embodiment, the tetrahydroprotoberberine (THPB), is l-stepholidine (l-SPD) and/or l-tetrahydropalmatine (l-THP). In another embodiment, the composition modulates dopaminergic receptor activity. In another embodiment, the $K_{ATP}$ channel is a Kir 6.2 and/or SUR1 subtype. In a particular embodiment, the cell is a neuron. In a particular embodiment, the cell is a pancreas cell. In another embodiment, the effective dosage is about 100 μM THB. In another embodiment, the composition is administered by bath-application.

The present invention provides a pharmaceutical composition, comprising, a quantity of a tetrahydroberberine (THB) molecule, or a pharmaceutical equivalent, analog, derivative, and/or salt thereof, and a pharmaceutically acceptable carrier. In another embodiment, the tetrahydroberberine (THB), or a pharmaceutical equivalent, analog, derivative, or salt thereof is a tetrahydroprotoberberine (THPB). In another embodiment, the tetrahydroprotoberberine (THPB) is l-stepholidine (l-SPD), or l-tetrahydropalmatine (l-THP).

The present invention provides a method of enhancing an overall drug treatment regimen in a subject, comprising, providing a composition comprising tetrahydroberberine (THB) molecule, or a pharmaceutical equivalent, analog, derivative, and/or salt thereof, and selectively inhibiting $K_{ATP}$ channel signaling by administering an effective dosage of a composition comprising tetrahydroberberine (THB) molecule, or a pharmaceutical equivalent, analog, derivative, and/or salt thereof to the subject. In another embodiment, the tetrahydroberberine (THB), or a pharmaceutical equivalent, analog, derivative, or salt thereof is a tetrahydroprotoberberine (THPB). In another embodiment, the tetrahydroprotoberberine (THPB), is l-stepholidine (l-SPD) and/or l-tetrahydropalmatine (l-THP). In another embodiment, the tetrahydroberberine (THB), or a pharmaceutical equivalent, derivative, analog, and/or salt thereof selectively inhibits $K_{ATP}$ channel signaling minimizes undesirable side effects as part of the overall drug treatment regimen. In another embodiment, the subject is a human. In another embodiment, the subject is a rat and/or mouse.

BRIEF DESCRIPTION OF THE FIGURES

Exemplary embodiments are illustrated in referenced figures. It is intended that the embodiments and figures disclosed herein are to be considered illustrative rather than restrictive.

FIG. 1 depicts different members of the THPB family of molecules in accordance with various embodiments of the invention. A: Depiction of the chemical structure of tetrahydroberberine (THB). B: Depiction of the chemical structure of l-tetrahydropalmatine (l-THP). C: Depiction of the chemical structure of l-tetrahydropalmatine (l-SPD).

FIG. 3 depicts THB restored rotenone-induced DA neuron hyperpolarization in accordance with various embodiments of the invention. A: Under current-clamp recording configuration, 1 μM rotenone induced a gradual membrane hyperpolarization, which was restored by a classical $K_{ATP}$ channel blocker, tolbutamide (100 μM, indicated by horizontal open bars above the trace). B: The $K_{ATP}$ channel opener, dizoxide (300 μM), also hyperpolarized membrane potential. C: Bath-application with THB alone moderately depolarized membrane potential accompanied with an increase in action potential firing. D: THB restored rotenone induced hyperpolarization. The horizontal dashed lines indicate the level of resting potential.

FIG. 8 depicts the effect of THB on $K_{ATP}$ channels in accordance with various embodiments of the invention. A: HEK-293 cells were transiently transfected to express $K_{ATP}$ (Kir6.2SUR1) channels and typical result of 100 μm THB antagonism is observed in single channel open probability compared to control. B: Normalized fold changes as a result of THB administration, with * indicating statistically significant difference (p<0.05) across three repeated experiments.

DETAILED DESCRIPTION OF THE INVENTION

Figure 2:
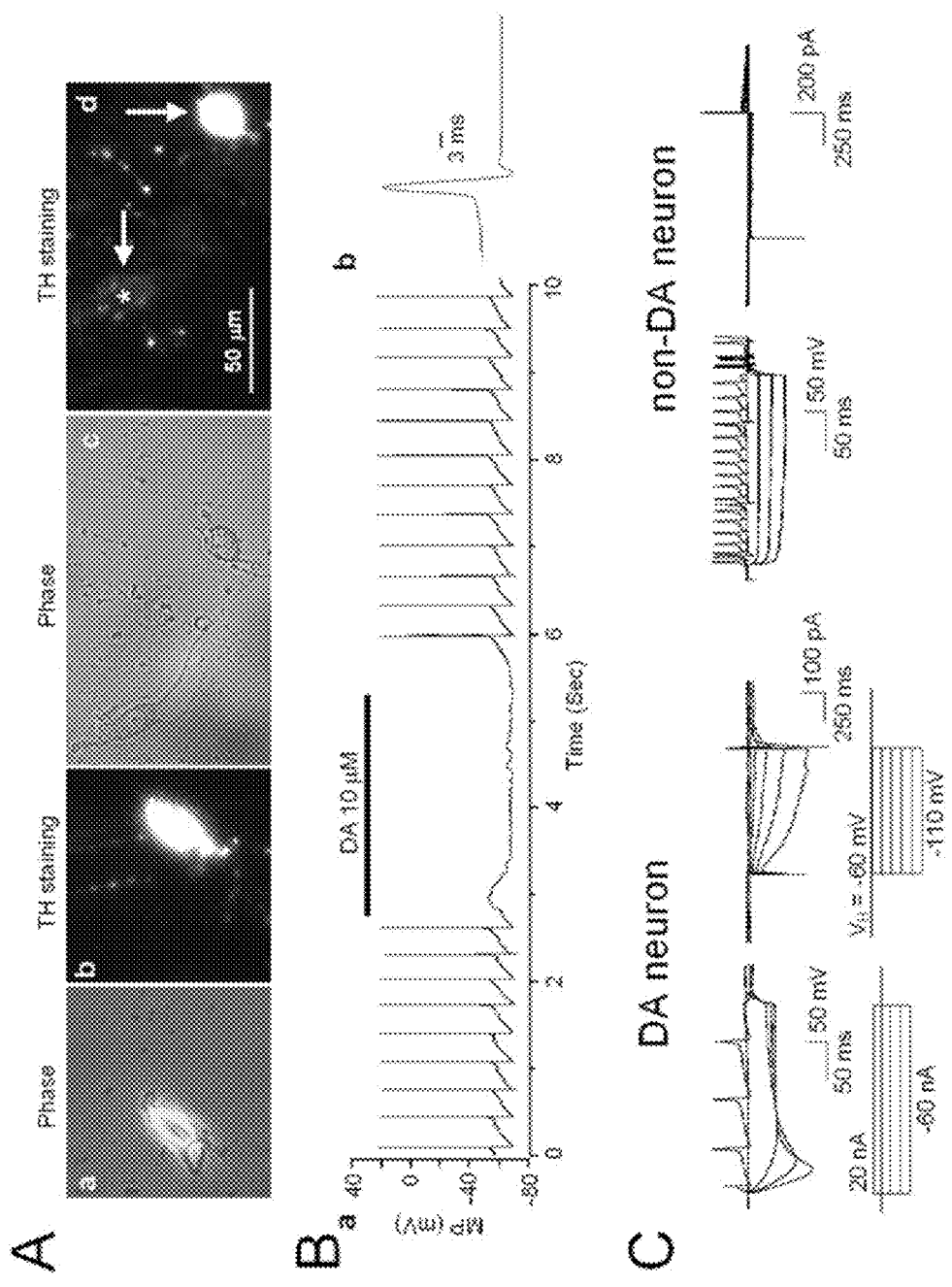
FIG. 2 depicts SNc DA neurons have distinct electrophysiological and pharmacological properties in accordance with various embodiments of the invention. A: TH staining of dissociated SNc DA neurons showed positive (Ab, d indicated by arrow) and negative (Ad indicated by asterisk) neurons. B: spontaneous firing of a SNc neuron was reversibly depressed by 10 μM dopamine (Ba). Bb showed a single action potential with extended time scale. C: In DA neurons, the hyperpolarizing induced current (Ih) can be induced under current-clamp or voltage-clamp condition.

All references cited herein are incorporated by reference in their entirety as though fully set forth. Unless defined otherwise, technical and scientific terms used herein have the same meaning as commonly understood by one of ordinary skill in the art to which this invention belongs. Singleton et al., *Dictionary of Microbiology and Molecular Biology* 3$^{rd}$ ed., J. Wiley & Sons (New York, N.Y. 2001); March, *Advanced Organic Chemistry Reactions, Mechanisms and Structure* 5$^{th}$ ed., J. Wiley & Sons (New York, N.Y. 2001); and Sambrook and Russel, *Molecular Cloning: A Laboratory Manual* 3rd ed., Cold Spring Harbor Laboratory Press (Cold Spring Harbor, N.Y. 2001), provide one skilled in the art with a general guide to many of the terms used in the present application.

One skilled in the art will recognize many methods and materials similar or equivalent to those described herein, which could be used in the practice of the present invention. Indeed, the present invention is in no way limited to the methods and materials described.

As used herein, the term "THB" means tetrahydroberberine. THB analogs and derivatives thereof include tetrahydroprotoberberines. As used herein, "THPB" tetrahydroprotoberberines means members of the tetrahydroprotoberberine family of molecules.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

"Treatment" or "treating" refers to therapy, prevention or prophylaxis and particularly refers to the administration of medicine or the performance of medical procedures with respect to a subject. Treatment may be for prophylactic purposes to reduce the extent or likelihood of occurrence of a disease state, disorder or condition. Treatment may also be for the purpose of reducing or eliminating symptoms of an existing disease state, disorder, condition, or undesirable appearance. Treatment may directly eliminate infectious agents or other noxious elements causing a disease state, disorder or a condition. Treatment may alternatively occur through enhancement and stimulation of an organism's natural immune system, such as promoting or facilitating repair and regeneration of damaged or disease cells and/or tissue. Treatment may also occur by supplementing or enhancing the body's normal function.

"Subject" or "patient" refers to a mammal, including a human, in need of treatment for a condition, disorder or disease.

"Neurodegenerative disease" refers to a disease or condition associated with diminished structure or function of the central, peripheral, and enteric nervous systems. Examples include: Alzheimer's disease, Frontotemporal dementia, Prion disorders, Parkinson's disease, Dementia with Lewy bodies, Corticobasal degeneration, Progressive supranuclear palsy, Huntington's disease, Multiple system atrophy, Amyotrophic lateral sclerosis, Spinal muscular atrophy, Hereditary spastic paraparesis, Spinocerebellar atrophies, Friedreich's ataxia, Amyloidoses, Multiple Sclerosis, Charcot Marie Tooth, among others.

Tetrahydroberberine (THB) is an alkaloid belonging to a group of molecules known as tetrahydroprotoberberines (THPB), wherein members of the THPB group share a common structure of an isoquinoline ring and methoxyl groups or hydrol groups at positions $C_2$, $C_3$, $C_9$, and $C_{10}$ (FIG. 1). (see U.S. Pat. No. 7,341,745). A proven source of THB and THPB molecules, as provided by the traditional medicine knowledge of East Asian countries such as China and Japan, are species of the *Corydalis, Stephania*, and *Fibraurea* genus of plants. Extracts from the flowering tuberous plant, *Corydalis ambigua* has long been used as an analgesic and sedative in East Asian medicinal techniques. However, it has been largely unclear what specific role THB, or related THPB molecules, play in providing such palliative medicinal effects. Studies have provided lines of evidence for THPB molecular interactions with D1 and D2 dopaminergic receptors [2, 3, 5, 7, 9, 10, 22, 23, 25, 37, 38, 40], α-adrenergic receptor [16], 5-TH receptor [17], Ca2+ channels [14, 17, 21] and K+ channels [30-32]. In this regard, there is improved understanding of molecular targets of certain THPB molecules, such as tetrahydropalmatine (THP); this knowledge has enabled synthetic manufacturing techniques and improvements in drug efficacy through generation of molecules such as enantiomeric levo-THP (l-THP). In contrast, the molecular targets of THB are almost entirely unknown. Deciphering the basis for THB biological activity provides an opportunity to improve manufacturing production techniques, engage in rational drug design, while discovering new therapeutic applications for THB.

The interactions of THP and l-THP with D1 and D2 dopaminergic receptors suggests the possibility of similar interactions for related molecule, THB. Dopaminergic receptors are a class of metabotropic G protein-coupled receptors prominent in the vertebrate central nervous system (CNS). Loss and dysfunction of these receptors are associated with a variety of neuropsychiatric disorders and neurodegenerative diseases, most notably Parkinson's disease, wherein death and degeneration of dopamine-containing cells of the substantia nigra in the brain are associated with a progressive loss of cognitive function and motor control. Dopamine receptors play a further role in cardiac function and regulation and in the renal system, through regulation of smooth muscle tissue found in blood vessels and enteric neuron signaling.

As suggested by other earlier described studies, THPB molecules modulate not only receptors, but ion channels present in the cells, including calcium channels [14, 17, 21] and potassium channels [30-32]. However, the nature of this activity, the means by which it is achieved, and the degree of THPB molecular activity on ion channel function is poorly understood. For THB, modulation of ion channel function is almost entirely unknown. Importantly, ion channels, including potassium channels, contain multiple subunits that are differentially expressed in tissues. Demonstrating selectivity of THB and THPB molecules towards specific subunit(s) would provide a critical opportunity to therapeutically target drug activity towards specific tissues and organs, while minimizing potentially undesirable side effects by eliminating activity in other types of tissues and organs.

Thus, establishing the interaction of THB with receptors and ion channels present in the cell, may open up new therapeutic applications, while aiding understanding of the precise biochemical properties of THB in modulating receptor function and cellular activity.

As disclosed herein, the targets and underlying mechanisms of THB are largely unknown. However, the inventors believed that THB blocks $K_{ATP}$ channels in dopaminergic (DA) neurons acutely dissociated from rat SNc. Using perforated patch-clamp recording in current-clamp mode, the functional $K_{ATP}$ channels can be opened by persistent perfusion of an inhibitor of complex I of the mitochondrial respiratory chain, rotenone. Bath-application of THB reversibly blocks opened $K_{ATP}$ channels in a concentration-dependent manner, which is comparable to a classical $K_{ATP}$ channel blocker, tolbutamide. Compared to THB analogs, l-stepholidine (l-SPD) or l-tetrahydropalmatine (l-THP), the THB's effect on the blockade of $K_{ATP}$ channels is more profound. In addition, exposure of only THB to the recorded neuron significantly increases action potential firing, and co-exposure of THB and dopamine restores dopamine-induced membrane hyperpolarization, demonstrating that THB exhibits an excitatory effect on SNc DA neurons through an antagonism of both D2 receptor and $K_{ATP}$ channels. Collectively, the blockade of neuronal $K_{ATP}$ channels by THB in SNc DA neurons is a novel pharmacological mechanism of THB, contributing to its neuroprotective effects in PD.

The potent activity of THB as a $K_{ATP}$ channel blocker, rivaling even that of classic blockers such as tolbutamide, is an important discovery towards new therapeutic avenues for THB, THB analog and derivatives, and THPB molecules. In particular, $K_{ATP}$ channels are octamers containing eight protein subunits, four of which are Kir6 (Kir 6.1 or 6.2) inward-rectifier potassium ion channels, with the other four subunits being sulfonylurea receptors (SUR1, SUR2A or SUR2B). Differential expression of these genes and thus the composition of $K_{ATP}$ channels in a particular cell, is directly linked to the metabolic environment where the cell is located. For example, high glucose levels induce a significant decrease in Kir 6.2 transcripts, which leads to closing of the channel, thereby modifying $K_{ATP}$ function. As a result of the metabolic environment for pancreatic cells, the predominant composition of $K_{ATP}$ channels found in β-cells is Kir 6.2/SUR1, whereas cardiac tissue largely possesses Kir 6.2/SUR2A and smooth muscle tissue possess Kir 6.2/SUR2B. Together, the dynamic modification of $K_{ATP}$ composition directly connected to the immediate surrounding environment provides a mechanism for cells to possess features compatible with their surrounding environment in tissue, towards performing specific biological functions.

Illustrating this principle, type-2 diabetes usually begins with insulin resistance, a disorder in which cells do not use insulin properly. As the need for insulin rises, the pancreas gradually loses its ability to produce insulin. In pancreatic β-cells, $K_{ATP}$ channels play a critical role in the regulation of β-cell excitation and insulin secretion. The closing of $K_{ATP}$ channels causes β-cell depolarization, in turn activates voltage-sensitive Ca2+ channels and increases cytosolic Ca2+ concentrations, thereby leading to insulin secretion. Therefore, many $K_{ATP}$ channel closers, including tolbutamide, glyburide, gliclazide, nateglinide, repaglinide and glibenclarimade, have been used for many years for the treatment of type-2 diabetes. However, as $K_{ATP}$ channels are widely expressed in a variety of tissues including cardiovascular cells, muscle cells, pancreatic β-cells and in various brain neurons, and the diversity of tissue-specific expression of SUR subunits may determine the pharmacological properties of $K_{ATP}$ channels. The diverse expression of $K_{ATP}$ channel subunits in different tissues causes possible side effects of oral diabetic drugs (sulfonylureas). Generally, sulfonylureas such as tolbutamide bind to $K_{ATP}$ channels in cellular membranes and in pancreatic beta cells inhibit a tonic, hyperpolarizing efflux of potassium. The result is an increasing positive electric potential over the membrane, resulting in depolarization causing opening voltage-gated Ca2+ channels. Within pancreatic cells, the rise in intracellular calcium leads to increased fusion of insulin granulae with the cell membrane, and therefore increased secretion of (pro)insulin.

For instance, it is believed that in the heart, $K_{ATP}$ channels play an important role in the intrinsic mechanisms that protect cardiac muscle during hypoxia/ischemia. In arterial smooth muscle, $K_{ATP}$ channels are also important in maintaining contractile tone, in turn controlling blood pressure and blood flow. It has been reported that in type-2 diabetic patients treated with sulfonylureas ($K_{ATP}$ channel blockers), the major cause of death is cardiovascular diseases, which could, at least in part, be relevant to the side effects of sulfonylureas by blocking cardiovascular $K_{ATP}$ channels. Therefore, the optimal, new generation of sulfonylureas is the drug that blocks pancreatic β-cell $K_{ATP}$ channels but exhibits little blocking effects on cardiovascular $K_{ATP}$ channels, or even better, that opens cardiovascular $K_{ATP}$ channels. Until now, there has been no such optimal drug to meet these purposes.

Figure 13:
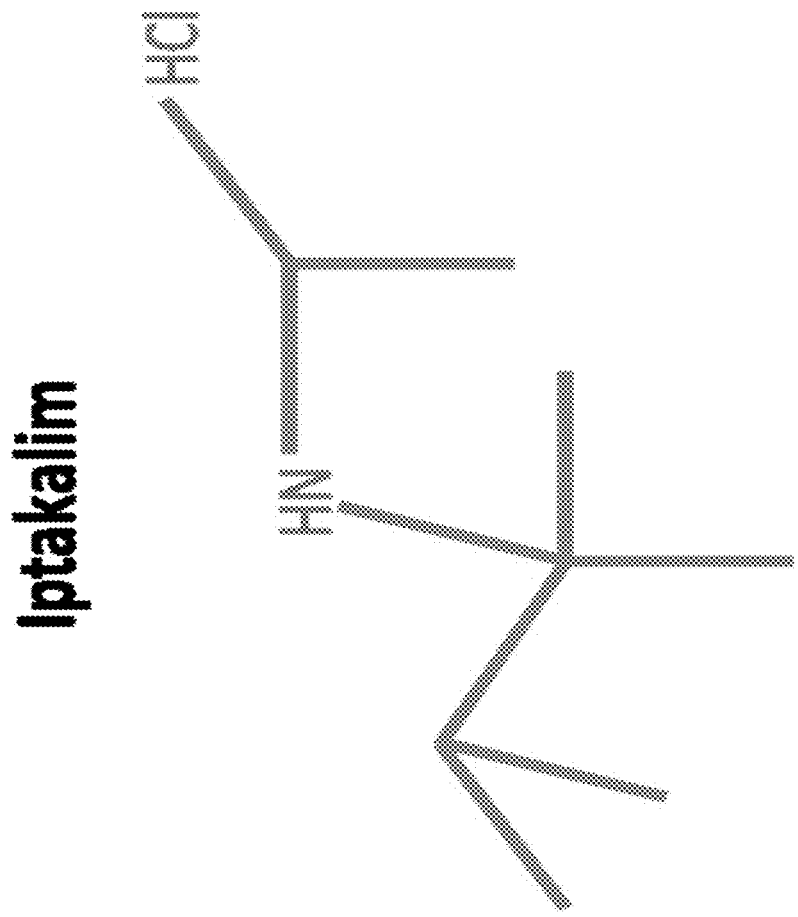
FIG. 13 depicts the chemical structure of Ipt.

Iptakalim (Ipt) is a novel cardiovascular $K_{ATP}$ channel opener initially designed and synthesized as an antihypertensive drug and has exhibited remarkable antihypertensive effects in a variety of hypertensive animal models using in vivo and in vitro preparations. The structure of Ipt can be viewed in FIG. 13. The molecular mechanisms underlying its antihypertensive effect include the activation of vascular $K_{ATP}$ channels. The inventors' previous work suggests that Ipt exhibits $K_{ATP}$ channel subunit selectivity. With relevant low concentration (<10 μM), it mainly opens vascular $K_{ATP}$ channels (Kir6.1SRU2B), weakly opens cardiac $K_{ATP}$ channels (Kir6.1SUR2A), which is its underlying mechanism to reduced blood pressure. However, with relatively high concentrations (>30 µM), it blocks neuronal type and pancreatic type of $K_{ATP}$ channels (Kir6.2SUR1). In addition, Ipt has been found to improve insulin resistance in type-2 diabetic animals. This pharmacological feature suggest that Ipt plays a beneficial effect in treating type-2 diabetes, especially if it combines with another pancreatic $K_{ATP}$ channel blocker.

In one embodiment, the present invention provides a method of treating a condition and/or disease associated with $K_{ATP}$ channel signaling by administering a therapeutically effective amount of a composition comprising THB, THB derivative or analog, member of the THPB group of molecules, Ipt, pharmaceutical equivalent and/or salt thereof, to a subject, where the composition comprising THB, THB derivative or analog, member of the THPB group of molecules, Ipt, pharmaceutical equivalent and/or salt thereof, results in the inhibition or decrease of $K_{ATP}$ channel signaling. In various embodiments, the concentration of THB and/or Ipt is about 10 µM, about 20 µM, about 50 µM, about 75 µM, about 100 µM, about 150 µM, about 200 µM, about 250 µM, about 300 µM, about 350 µM, about 400 µM, about 450 µM, about 500 µM or greater than about 500 µM. In some embodiments, a pharmaceutical composition comprising a Ipt and THB or derivatives thereof, can be administered to treating a condition and/or disease associated with $K_{ATP}$ channel signaling.

In another embodiment, the condition and/or disease is a neuropsychiatric, motorneuron or neurodegenerative disease. In another embodiment, the condition and/or disease is Parkinson's disease. In another embodiment, the subject is a human. In another embodiment, the subject is a rat or mouse. In another embodiment, the $K_{ATP}$ channel is in a neuron. In another embodiment, the $K_{ATP}$ channel is in a dopaminergic (DA) neuron. In various embodiments, the $K_{ATP}$ channel consists of a Kir 6.1 or Kir 6.2 subunit. In various embodiments, the $K_{ATP}$ channel consists of a SUR1, SUR2A or SUR2B subunit.

In one embodiment, the present invention provides a method of treating diabetes by administering a therapeutically effective amount of a composition comprising Ipt, THB, THB derivative or analog, member of the THPB group of molecules, pharmaceutical equivalent and/or salt thereof, to a subject. In another embodiment, the administration of the composition comprising Ipt, THB, THB derivative or analog, member of the THPB group of molecules, pharmaceutical equivalent and/or salt thereof results in the closing of one or more $K_{ATP}$ channels in a pancreatic β-cell. In another embodiment, the administration of the composition comprising Ipt, THB, THB derivative or analog, member of the THPB group of molecules, pharmaceutical equivalent and/or salt thereof results the opening of one or more cardiovascular $K_{ATP}$ channels. In another embodiment, the subject is a human. In another embodiment, the subject is a rat or mouse. In another embodiment, the $K_{ATP}$ channel is in a pancreatic cell. In another embodiment, the $K_{ATP}$ channel is in a pancreatic β-cell. In various embodiments, the $K_{ATP}$ channel consists of a Kir 6.1 or Kir 6.2 subunit. In various embodiments, the $K_{ATP}$ channel consists of a SUR1, SUR2A or SUR2B subunit.

In some embodiments, the present disclosure may comprises providing a method of treating diabetes by administering a therapeutically effective amount of a composition comprising at least two of: Ipt, THB, THB derivative or analog, member of the THPB group of molecules, pharmaceutical equivalent and/or salt thereof, to a subject. For example, in some embodiments, the combination may comprise Ipt and THB, each in therapeutically effective amounts within the composition. In particular, in some aspects, the Ipt and THB are in generally similar proportions within the pharmaceutical composition and in other embodiments, one active ingredient may comprise a greater proportion of mass compared to the other active ingredient.

In one embodiment, the present invention provides a method of treating atherosclerosis, congestive heart failure or other cardiovascular disease by administering a therapeutically effective amount of a composition comprising Ipt, THB, THB derivative or analog, member of the THPB group of molecules, pharmaceutical equivalent and/or salt thereof, to a subject. In another embodiment, the administration of the composition comprising Ipt, THB, THB derivative or analog, member of the THPB group of molecules, pharmaceutical equivalent and/or salt thereof results in the opening of one or more $K_{ATP}$ channels in a cell found in cardiac tissue or blood vessels near cardiac tissue. In another embodiment, the administration of the composition comprising Ipt, THB, THB derivative or analog, member of the THPB group of molecules, pharmaceutical equivalent and/or salt thereof results the opening of one or more cardiovascular $K_{ATP}$ channels. In another embodiment, the subject is a human. In another embodiment, the subject is a rat or mouse. In various embodiments, the $K_{ATP}$ channel consists of a Kir 6.1 or Kir 6.2 subunit. In various embodiments, the $K_{ATP}$ channel consists of a SUR1, SUR2A or SUR2B subunit.

In various embodiments, the present invention provides pharmaceutical compositions including a pharmaceutically acceptable excipient along with a therapeutically effective amount of Ipt, THB, THB derivative or analog, member of the THPB group of molecules, pharmaceutical equivalent and/or salt thereof. In one embodiment, the composition comprises THB analogs l-tetrahydropalmatine (l-THP) and/or l-stepholidine (l-SPD). "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal or parenteral. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders.

The pharmaceutical compositions according to the invention can also contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, for instance, by monitoring a subject's response to administration of a compound and adjusting the dosage accordingly. For additional guidance, see *Remington: The Science and Practice of Pharmacy* (Gennaro ed. 20th edition, Williams & Wilkins PA, USA) (2000).

Typical dosages of an effective composition comprising Ipt, THB, THB derivative or analog, member of the THPB group of molecules, pharmaceutical equivalent and/or salt thereof can be in the ranges recommended by the manufacturer where known therapeutic compounds are used, and also as indicated to the skilled artisan by the in vitro responses or responses in animal models. Such dosages typically can be reduced by up to about one order of magnitude in concentration or amount without losing the relevant biological activity. Thus, the actual dosage will depend upon the judgment of the physician, the condition of the patient, and the effectiveness of the therapeutic method based, for example, on the in vitro responsiveness of the relevant primary cultured cells or histocultured tissue sample, or the responses observed in the appropriate animal models, as previously described. In various embodiments, the concentration of Ipt and/or THB is about 10 µM, about 20 µM, about 50 µM, about 75 µM, about 100 µM, about 150 µM, about 200 µM, about 250 µM, about 300 µM, about 350 µM, about 400 µM, about 450 µM, about 500 µM or greater than about 500 µM.

As readily apparent to one of skill in the art, embodiments of the invention may be applicable to any number of conditions and/or diseases associated with ATP-sensitive potassium ($K_{ATP}$) channels, and the invention is in no way limited to only treating Parkinson's disease or diabetes. Similarly, as readily apparent to one of skill in the art, the various embodiments described herein are not in any way limited to THB and/or Ipt. Any Ipt or THB related compound, derivative, analog, member of the THPB group of molecules, pharmaceutical equivalent and/or salt thereof, that may also result in the inhibition or blockage of $K_{ATP}$ channels may also be used in conjunction with the various embodiments herein.

One skilled in the art will recognize many methods and materials similar or equivalent to those described herein, which could be used in the practice of the present invention. Indeed, the present invention is in no way limited to the methods and materials described. For purposes of the present invention, the following terms are defined below.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Generally

The targets and underlying mechanisms of tetrahydroberberine (THB) are largely unknown. However, the inventors believed that THB blocks $K_{ATP}$ channels in dopaminergic (DA) neurons acutely dissociated from rat SNc. Using perforated patch-clamp recording in current-clamp mode, the functional $K_{ATP}$ channels can be opened by persistent perfusion of an inhibitor of complex I of the mitochondrial respiratory chain, rotenone. Bath-application of THB reversibly blocks opened $K_{ATP}$ channels in a concentration-dependent manner, which is comparable to a classical $K_{ATP}$ channel blocker, tolbutamide.

Compared to THB analogs, l-stepholidine (l-SPD) or l-tetrahydropalmatine (l-THP), the THB's effect on the blockade of $K_{ATP}$ channels is more profound. In addition, exposure of only THB to the recorded neuron significantly increases action potential firing, and co-exposure of THB and dopamine restores dopamine-induced membrane hyperpolarization, demonstrating that THB exhibits an excitatory effect on SNc DA neurons through an antagonism of both D2 receptor and $K_{ATP}$ channels. Collectively, the blockade of neuronal $K_{ATP}$ channels by THB in SNc DA neurons is a novel pharmacological mechanism of THB, contributing to its neuroprotective effects in PD.

Example 2

Single DA Neuron Dissociation from Rat SNc

The protocol for preparation of single neurons from the rat SNc was approved by the Institutional Animal Care and Use Committee of the Barrow Neurological Institute. Single DA neurons were acutely dissociated from the SNc of 2-3-week-old Wistar rats following the protocol as previously described [28, 29, 34]. Briefly, rats were anesthetized with isoflurane, and brain tissue was rapidly removed and immersed in cold (2-4° C.) dissection solution which contained: 136.7 mM NaCl, 5 mM KCl, 0.1 mM Na2HPO4, 0.2 mM KH2PO4, 9.84 mM HEPES, 16.6 mM D-glucose, 21.9 mM sucrose, pH 7.3, 330 mOsm, oxygenated with 100% O2 [8]. Three 400-μm coronal slices containing the SNc were cut using a vibrotome (Vibroslice 725M, WPI, Sarasota, Fla.). After cutting, slices were continuously bubbled with 95% O2-5% CO2 at room temperature (22±1° C.) for at least one hour in artificial cerebrospinal fluid (ACSF), which contained: 124 mM NaCl, 5 mM KCl, 24 mM NaHCO3, 1.3 mM MgSO4, 1.2 mM KH2PO4, 2.4 mM CaCl2, and 10 mM glucose, pH 7.4. Thereafter, slices were treated with pronase (1 mg per 6 ml) at 31° C. for 30 minutes in ACSF. The SNc was identified in a coronal slice using a stereo microscope with reference to the rat brain atlas [19], and was micro-punched out from slices using a well-polished needle. One punched piece was then transferred to a 35-mm culture dish filled with well-oxygenated standard extracellular solution, which contained: 150 mM NaCl, 5 mM KCl, 1 mM MgCl2, 2 mM CaCl2, 10 mM glucose 10, and 10 mM HEPES, pH 7.4 (with Tris-base). The punched piece was then dissociated mechanically using a fire-polished micro-Pasteur pipette under an inverted microscope (Olympus IX-70, Lake Success, N.Y.). The separated cells adhered to the bottom of the culture dish within 30 minutes. In the present study, we used only DA neurons that maintained their original morphological features of polygonal, large or medium somata with 2-4 thick primary dendritic processes were used.

Example 3

Perforated Patch-Clamp Whole-Cell Recordings

Perforated patch whole-cell recording techniques were employed as previously described [28, 29, 34]. Pipettes (3-5 MΩ) used for perforated patch recording were filled with intracellular recording solution containing 140 mM potassium gluconate, 10 mM KCl, 5 mM MgCl2, and 10 mM HEPES, pH 7.2 (with Tris-OH). The amphotericin B was freshly prepared to 200-240 μg/ml from a 40 mg/ml in DMSO stock. The liquid junction potential was 14 mV calculated using Clampex 9.2 (Axon Instruments, Foster City, Calif.) and corrections were made for junction potentials post-hoc. After tight seal (>2 GΩ) formation, it usually took about 5-20 min to convert to perforated patch mode, and an access resistance of 20-60 MΩ was accepted to start the experiments. Series resistance was not compensated in this study. The data were filtered at 2 kHz, acquired at 10 kHz and digitized on-line (Digidata 1322 series A/D board, Axon Instruments, Foster City, Calif.). All data were displayed and stored on a PC computer. Drug application was performed using a computer-controlled "U-tube" system as previously described [28, 29, 32]. All experiments were performed at room temperature (22±1° C.). To enable identification of single, dissociated SNc neurons after a patch-clamp recording session, the recording pipette was filled with a fluorescent dye (lucifer yellow CH, Sigma Chemical Co., St. Louis, Mo., 1.0 mg/ml in the recording electrode) in some experiments. After conversion from the perforated patch to the conventional whole-cell recording mode, the dye was ejected into the cytoplasm by a pulse (200 ms, 0.5 Hz) of hyperpolarizing current (1.0 nA) for 3 min. Labeled cells were visualized using epifluorescence microscopy.

Example 4

Immunocytochemical Staining

Dissociated VTA neurons were fixed with 4% paraformaldehyde for 15 min, rinsed three times with PBS, and treated with Saponin (1 mg/ml) for 5 min to permeabilize the cells. After rinsing four times with phosphate-buffered saline, the neurons were incubated at room temperature in (TH) primary antibody (AB152, Chemicon International, Temecula, Calif.) diluted 1:1000 in Hank's balanced salt solution supplemented with 5% bovine serum albumin as a blocking agent for 30 min. Following another three rinses with phosphate-buffered saline, the secondary antibody (anti-mouse IgG cy3 conjugate, Sigma Chemical Co., St. Louis, Mo.) was applied at room temperature for 30 min (diluted 1:100). After rinsing a final three times with phosphate-buffered saline, the labeled cells were visualized using fluorescence microscopy.

Example 5

Chemicals and Statistics

Pronase was purchased from Calbiochem-Novabiochem Co (La Jolla, Calif., USA); rotenone, tolbutamide, and lucifer yellow were purchased from Sigma (St. Louis, Mo., USA). All other chemicals were purchased from Tocris Cookson, Inc. (Ballwin, Mo., USA), except THB, l-THP and l-SPD (FIG. 1). Differences in altered membrane potentials (mV) were tested by Student's paired two-tailed t test using the raw data. Numerical values are presented as the mean S.E.M. The probability values of $p<0.05$ were considered significant.

Example 6

Identification of Dissociated SNc DA Neurons

TH staining showed that the dissociated neurons from SNc exhibited TH positive (FIG. 2Ab, d) and negative (FIG. 2Ad*) reactions. For patch-clamp recording, DA neurons were identified early in the recording session based on previously described criteria [12]: (1) 1-3 Hz spontaneous action potential firing (FIG. 2Ba), (2) the duration of action potential is longer than 2.5 ms (FIG. 2Bb), (3) spontaneous action potential firing is eliminated by 10 μM DA (FIG. 2Ba), and (4) expression of a hyperpolarization-induced current (FIG. 2C). In some experiments, after patch-clamp recording, the fluorescence dye, Lucifer yellow (0.5 mg/ml) was delivered into recorded cell and labeled cell was stained with TH for further confirmation of DA neuronal phenotype (FIG. 2).

Example 7

Effects of the THB on Functional $K_{ATP}$ Channels in SNc DA Neurons

Under physiological conditions, the $K_{ATP}$ channels are mostly closed. However, in the acutely-dissociated single neurons from rat SNc, there is background opening of $K_{ATP}$ channels [29]. To open these $K_{ATP}$ channels, an inhibitor of complex I of the mitochondrial respiratory chain, rotenone (1 μM) was bath-applied to patch-recorded neuron under current-clamp recording mode. The opening of functional $K_{ATP}$ channels was evident as a gradual reduction of action potential firing and hyperpolarization of membrane potential (FIG. 3A). In 30 neurons tested, the averaged resting membrane potential was −46.1±0.9 mV, while after perfusion of 1 μM rotenone for 1-3 min, the membrane potential was hyperpolarized to −61.1±0.9 mV (p<0.001). In the presence of rotenone, the application of a classical $K_{ATP}$ channel blocker, tolbutamide (100 μM) quickly restored membrane potential hyperpolarization and fired action potential (FIG. 3A), suggesting an opening of $K_{ATP}$ channels by rotenone. Alternatively, the functional $K_{ATP}$ channels were also able to be opened by a $K_{ATP}$ channel opener, dizoxide (100 μM, FIG. 3B). Then, the inventors tested the effects of the THB on the opened $K_{ATP}$ channels. As shown in FIG. 3C, bath-perfusion of 100 μM THB increased firing rate of spontaneous action potential firing with a moderate membrane potential depolarization. Before and after exposure to 100 μM THB, the values of fairing rate were 1.4 and 2.2 Hz, respectively (p<0.05, n=7); and membrane potentials were −46.5±0.9 and −41.3±1.9 mV, respectively (p<0.05, n=7). Whereas a classical $K_{ATP}$ channel blocker tolbutamide (100 μM) showed little depolarization of membrane potential (from −44.4±1.6 to −44.1±1.8 mV, p>0.05, n=5). In the presence of rotenone, THB restored membrane potential hyperpolarization, which was comparable to 100 μM tolbutamide (FIG. 3D). During persistent perfusion of 1 μM rotenone, THB depolarized membrane potential from −61.7±1.3 to −46.7±0.9 mV (p<0.01, n=11) and tolbutamide depolarized potential from −61.6±1.2 to −52.5±1.1 (p<0.01, n=21). These results support THB blockage of $K_{ATP}$ channels in dissociated SNc DA neurons.

Example 8

Effects of THB Analogs on Functional $K_{ATP}$ Channels in SNc DA Neurons

Figure 4:
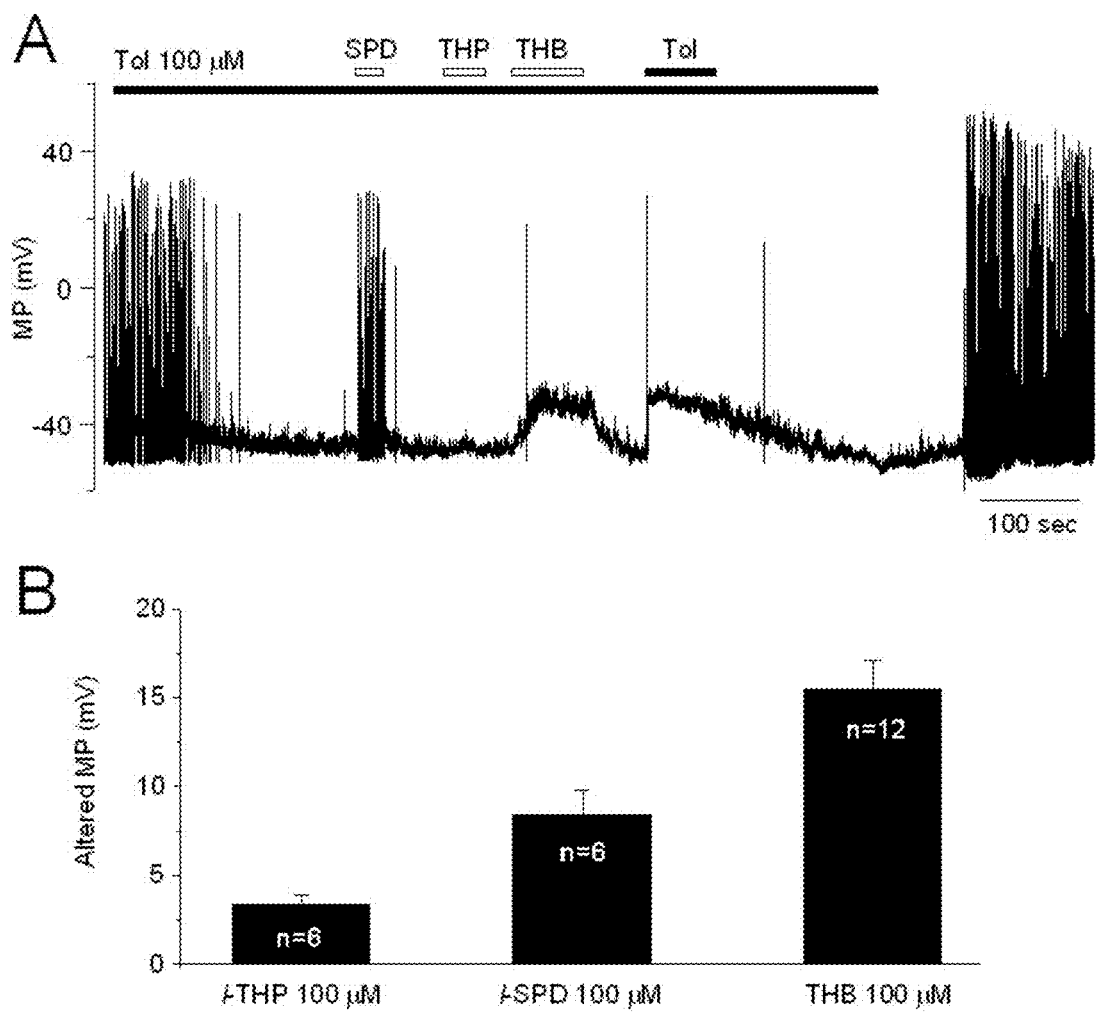
FIG. 4 depicts effects of THB analogs on rotenone-induced membrane hyperpolarization in accordance with various embodiments of the invention. A: Representative typical trace in a recorded SNc DA neuron, in which, l-SPD, l-THP, THB and tolbutamide was applied, respectively. B: Bar graph summarizes the blocked effect of THB analogs on rotenone-opened $K_{ATP}$ channels. The number in the each column indicated the neurons tested, and the vertical bars represent Mean±SEM.

With the same concentration (100 μM), THB induced more membrane depolarization than l-SPD, while l-THP exhibited little effect on opened $K_{ATP}$ channels (FIG. 4A). In 6 neurons tested, altered membrane potentials were 3.4±0.5, 8.4±1.4 and 15.5±1.6 mV for 100 μM l-THP, l-SPD and THB, respectively (p<0.01, FIG. 4B). These results support THB blockage of $K_{ATP}$ channels.

Example 9

Figure 5:
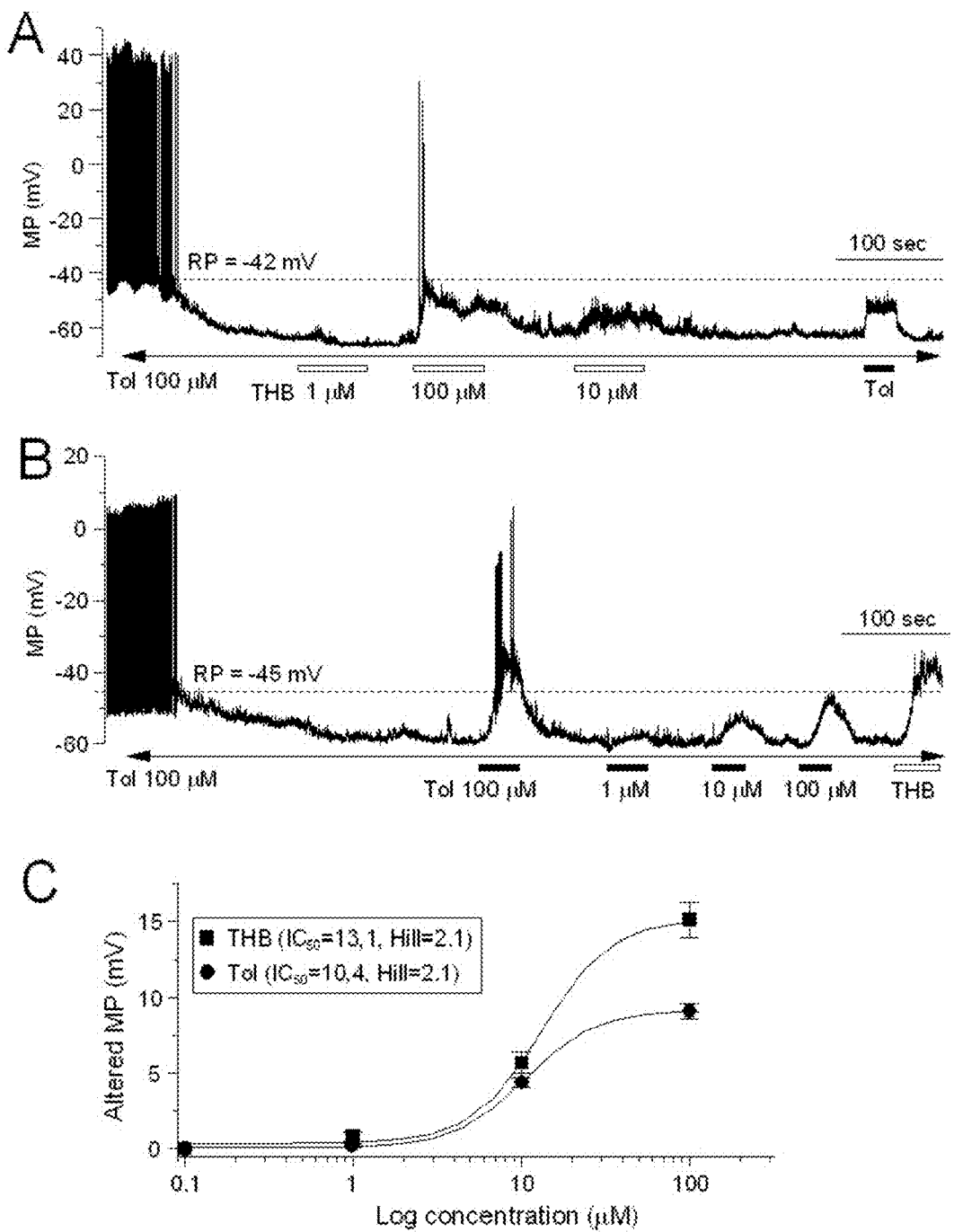
FIG. 5 depicts THB blocks $K_{ATP}$ channels in a concentration-dependent manner in accordance with various embodiments of the invention. A: Representative a typical trace of a recorded SNc DA neuron, in which, different concentrations of THB were applied. B: Representative a typical trace of a recorded SNc DA neuron, in which, different concentrations of tolbutamide were applied. C: Comparison of concentration-effect relationship between THB and tolbutamide. THB showed more potent inhibition than tolbutamide in opened $K_{ATP}$ channels. Each symbol was averaged from 11-21 neurons tested, and the vertical bars represent Mean±SEM.

THB Blocks $K_{ATP}$ Channels in SNc DA Neurons in a Concentration-Dependent Manner To evaluate the affinity of THB on $K_{ATP}$ channels, the concentration-effect relationship was examined. The results demonstrated that THB (FIG. 5A) depolarized membrane potential in a concentration-dependent manner in the presence of rotenone, which is comparable to tolbutamide (FIG. 5B). The altered membrane potentials were 0.8±0.3 (n=11), 5.7±0.7 (n=11) and 15.1±1.2 mV (n=12) for 1, 10 and 100 μM THB, and that values were 0.2±0.1 (n=14), 4.4±0.3 (n=14) and 9.1±0.5 mV (n=21) for 1, 10 and 100 μM tolbutamide, respectively (FIG. 5C). The difference of membrane depolarization induced by 100 μM THB and tolbutamide was significant (15.1±1.2 mV vs. 9.1±0.5 mV, p<0.05). The concentration-effect relationship curves showed that the IC50 and Hill coefficient were 13.1 μM and 2.1 for THB (n=11), and 10.4 and 2.1 for tolbutamide. These results support THB blockage of $K_{ATP}$ channels in a concentration-dependent manner. Compared to tolbutamide, THB exhibits similar affinity but more potent block of $K_{ATP}$ channels.

Example 10

Figure 6:
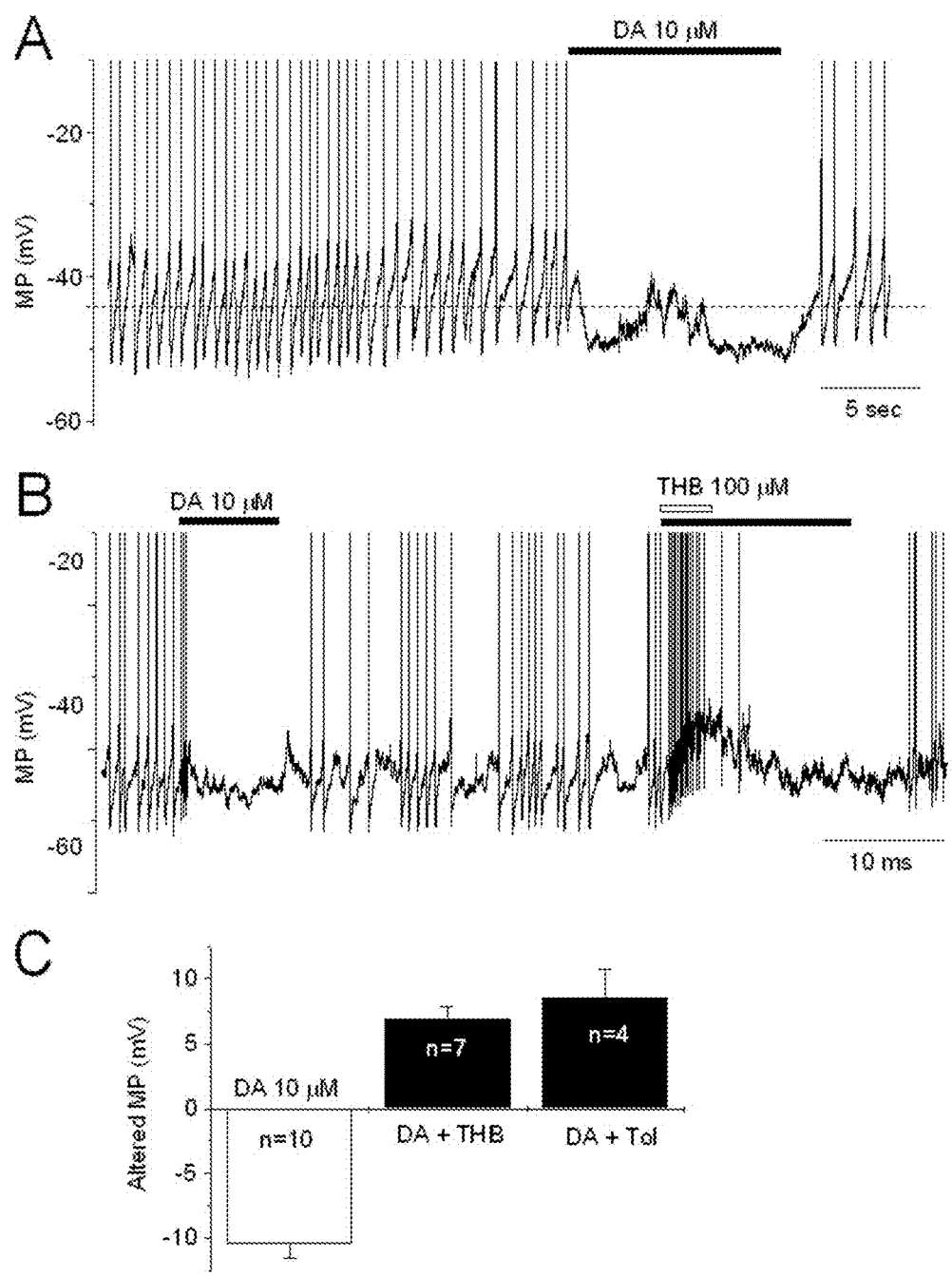
FIG. 6 depicts effects of THB on dopamine-induced membrane hyperpolarization in accordance with various embodiments of the invention. A: In dissociated DA neurons from the SNc, application of DA hyperpolarized membrane potential. B: Co-application of DA with THB abolished DA-induced membrane hyperpolarization. C: Summary of the effects of DA, THB and tolbutamide on membrane potentials.

Comparison of Effects of THB and Tolbutamide on Dopamine-Opened K+ Channels Results described herein indicate that THB exhibits more profound effects on opened $K_{ATP}$ channels than tolbutamide (15.1±1.2 mV vs. 9.1±0.5 mV, p<0.05). One possible interpretation is that the THB is the D2 receptor antagonist, which blocks D2-associated K+ channels in addition to $K_{ATP}$ channels. To test this possibility, the inventors compared the effects of THB and tolbutamide on dopamine-induced membrane potential hyperpolarization (through the activation of D2 receptor and consequent opening of K+ channels). In 10 neurons tested, bath-application of 10 μM dopamine hyperpolarized membrane potential of 10.5±1.1 mV, p<0.01). Co-application of dopamine with 100 μM THB depolarized membrane potential from −45.6±1.0 to −38.6±1.2 mV, p<0.001, n=7), while tolbutamide depolarized membrane potential from −45.3±2.3 to 36.8±3.8 mV, p<0.05, n=4) (FIG. 6C). The difference between altered membrane potentials between THB and tolbutamide was not significantly different (7.0±0.9 mV vs. 8.5±2.2 mV, p>0.05). These results demonstrate that the more potent blockade of $K_{ATP}$ channels by THB than that by tolbutamide is not caused by an additional effect of THB on D2 receptors.

Example 11

Figure 7:
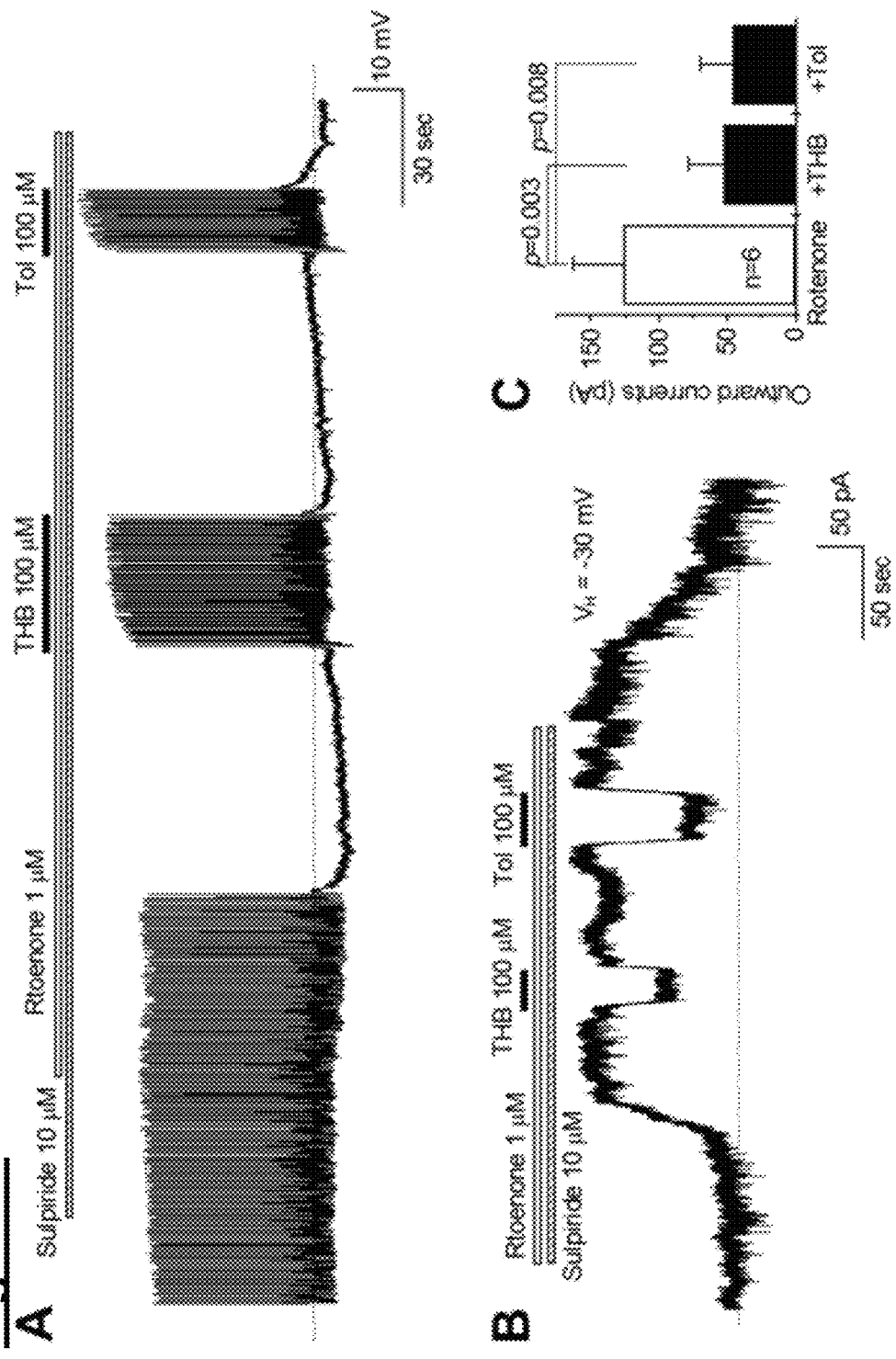
FIG. 7 depicts role of D2 receptors in THB's effect on rotenone-induced membrane hyperpolarization in accordance with various embodiments of the invention. A: In the presence of D2 receptor antagonist sulpiride, application of rotenone induced a membrane potential hyperpolarization, which was restored by either THB or tolbutamide (Tol). This is a typical trace representative of 6 neurons tested. B: Under a voltage clamp recording mode (VH ¼ 3530 mV), rotenone induced an outward current in the presence of D2 receptor antagonist, sulpiride. On the top of the outward current, addition of either THB or Tol significantly reduced the current amplitude. C: Summary of the effects of THB and Tol on rotenone-induced outward current in the presence of D2 receptor antagonist. The number inside of column indicates the cells tested.

Further Comparison of Effects of THB and Tolbutamide on Dopamine-Opened K+ Channels Further results showed that THB but not Tol restored D2 receptor-mediated hyperpolarization confirming THB does block D2 receptor function. Examining the effects of THB on rotenone-induced membrane hyperpolarization in the presence of D2 receptor antagonist, 6 neurons were tested. Bath-application of 1 mM rotenone hyperpolarized membrane potential in the presence of D2 receptor antagonist, sulpiride (10 mM) was applied. Under this condition (without functional D2 receptors), THB significantly restored membrane hyperpolarization and action potential firing (FIG. 7A). Exposure of silpiride alone did not clearly alter resting membrane potential although the neuronal firing rate was increased. These results support the idea that THB restores rotenone-induced hyperpolarization via a block of the opened $K_{ATP}$ channels. In addition, in the presence of sulpiride, rotenone induced an outward current response under voltage-clamp recording mode at a holding potential (VH) of −30 mV, and both THB and Tol inhibited this outward current, respectively (FIG. 7B). In 6 neurons tested, rotenone-induced outward currents exhibited an amplitude of 125.8±37.1 pA, which was reduced to 52.5±25.7 pA (p<0.01) and 45.8±23.7 pA (p<0.01) after addition of 100 mMTHB and 100 mM Tol, respectively (FIG. 7C). These results further confirm that like Tol, THB is an efficacious blocker for neuronal $K_{ATP}$ channels.

Example 12

Treatment of Conditions and Diseases Associated with $K_{ATP}$ Channel Signaling As described herein, direct electrophysiological evidence is provided that the $K_{ATP}$ channels in SNc DA neurons are the novel targets that mediate THB pharmacological effects. The inventors show that THB exhibits the most profound block of $K_{ATP}$ channels compared to its analogs l-SPD and l-THP. The inventors also demonstrate that THB inhibits $K_{ATP}$ channels in a concentration-dependent manner, and its inhibitory effect is more potent than the classical $K_{ATP}$ channel blocker tolbutamide. Considering the roles of $K_{ATP}$ channels in PD pathogenesis, these results open a new window for THB as a therapeutic drug for PD treatment, as well as treatment for any disease and/or condition associated with $K_{ATP}$ channel signaling.

Example 13

Effect of THB on $K_{ATP}$ Channel Signaling for Kir 6.2SUR1 Subtype

In β-cells, the dominant subtype of $K_{ATP}$ is the Kir 6.2SUR1 subtype, as earlier described. Cells transiently transfected with the $K_{ATP}$ Kir 6.2SUR1 channel subtype were evaluated for membrane potential and action potential firing using cell-attached recording in the presence or absence of 100 μm THB (FIG. 8A). Results across three experiment demonstrate THB antagonism, as demonstrated by a 50% change in channel activity $NP_0$ compared to control (FIG. 8B).

In further examples demonstrating THB antagonism of $K_{ATP}$ channels, membrane potential and action potential firing in native β-cells may be measured following application of THB. Similar results may be generated using cardiac or smooth muscle cell lines to demonstrate selectively of THB, THB analogs and derivatives or THPB molecules on various $K_{ATP}$ channel subtypes composed of Kir 6.1/6.2 and SUR1/2A/2B fractions. Selective activity of THB, THB analogs and derivatives or THPB molecules towards specific $K_{ATP}$ channels would establish biological activity of THB in particular cells and tissue types for a particular disease or condition of interest. Further confirmation of THB activity using in vivo models, for example animal models harboring mutations to recapitulate diabetes, would demonstrate an enhancement of drug efficacy via selective Kir 6.2/SUR1 activity, while minimizing undesirable side effects through elimination of activity in different cell and tissue types.

Example 14

Treatment of Diabetes with THB, or Derivative, Analog, Pharmaceutical Equivalent and/or Salt Thereof Type-2 diabetes usually begins with insulin resistance, a disorder in which cells do not use insulin properly. As the need for insulin rises, the pancreas gradually loses its ability to produce insulin. The purpose of type-2 diabetes treatment is to low or control circulating blood glucose levels through food management, exercise and medication. More than 50% of diagnosed type-2 diabetic patients need to take medication. Current strategies to treat diabetes include reducing insulin resistance using glitazones, supplementing insulin supplies with exogenous insulin, or increasing endogenous insulin production with sulfonylureas. Sulfonylureas constitute the leading oral antihyperglycaemic agents over the past halfcentury. The major target of sulfonylureas is one type of potassium ion channel, called ATP-sensitive potassium ($K_{ATP}$) channels, which are expressed in pancreatic β-cells. $K_{ATP}$ channels belong to a family of inwardly rectifying potassium channel subunits (Kir6.2 or 6.1) each coupled to a sulfonylurea (SUR) binding subunit. In pancreatic β-cells, $K_{ATP}$ channels play a critical role in the regulation of β-cell excitation and insulin secretion. The closing of $K_{ATP}$ channels causes β-cell depolarization, in turn activates voltage-sensitive Ca2+ channels and increases cytosolic Ca2+ concentrations, thereby leading to insulin secretion. Therefore, many $K_{ATP}$ channel closers, including tolbutamide, glyburide, gliclazide, nateglinide, repaglinide and glibenclarimade, have been used for many years for the treatment of type-2 diabetes.

$K_{ATP}$ channels are widely expressed in a variety of tissues including cardiovascular cells, muscle cells, pancreatic β-cells and in various brain neurons, and the diversity of tissue-specific expression of SUR subunits may determine the pharmacological properties of $K_{ATP}$ channels. Among these tissues, SUR subunits have shown different expression. For example, pancreatic β-cells express Kir6.2-SUR1, myocardial cells express Kir6.2-SUR2A, while smooth muscle cells of blood vessels express Kir6.1/6.2-SUR2B. Sulfonylureas block β-cell $K_{ATP}$ channels, while simultaneously blocking other tissues' $K_{ATP}$ channels, causing side effects during type-2 diabetes treatment.

The diverse expression of $K_{ATP}$ channel subunits in different tissues causes possible side effects of oral diabetic drugs (sulfonylureas). For instance, it is believed that in the heart, $K_{ATP}$ channels play an important role in the intrinsic mechanisms that protect cardiac muscle during hypoxia/ischemia. In arterial smooth muscle, $K_{ATP}$ channels are also important in maintaining contractile tone, in turn controlling blood pressure and blood flow. It has been reported that in type-2 diabetic patients treated with sulfonylureas ($K_{ATP}$ channel blockers), the major cause of death is cardiovascular diseases, which has been argued that this could, at least in part, be relevant to the side effects of sulfonylureas by blocking cardiovascular $K_{ATP}$ channels. Therefore, the optimal, new generation of sulfonylureas is the drug that blocks pancreatic β-cell $K_{ATP}$ channels but exhibits little blocking effects on cardiovascular $K_{ATP}$ channels, or even better, that opens cardiovascular $K_{ATP}$ channels. Until now, there has been no such optimal drug to meet these purposes.

Although tolbutamide (first generation of sulfonylureas) and gliclazide (second generation of sulfonylureas) were reported to produce high affinity closure of β-cell type (Kir6.2/SUR1), but not cardiac (Kir6.2/SUR2A) or smooth muscle type (Kir6.2/SUR2B), $K_{ATP}$ channels, they exhibit little opening effects on cardiovascular $K_{ATP}$ channels. The development of a new drug that closes pancreatic β-cell $K_{ATP}$ channels but opens cardiovascular $K_{ATP}$ channels has important clinical significances. Large amounts of evidence indicate that the opening of cardiovascular $K_{ATP}$ channels exhibits beneficial effects on cardiovascular disorders, including the protection of the myocardial system against ischemia/hypoxia, the prevention of ventricular arrhythmias and anti-hypertension. All of these $K_{ATP}$ channel-opening effects will benefit type 2-diabetic patients with accompanying cardiac and blood vessel disorders. Thus, a considerable need exists for a compound that can selectively block pancreatic β-cell $K_{ATP}$ channels but open cardiovascular $K_{ATP}$ channels, which will be an optimal therapeutic strategy to treat type-2 diabetes with positive benefits for cardiac and vessel systems.

As disclosed herein, the inventors discovered that that the tetrahydroberberine (THB) and its analog l-stepholidine (l-SPD) potently block functional $K_{ATP}$ channels natively expressed on midbrain dopamine neurons. The similarity of $K_{ATP}$ channel subunit composition (Kir6.2SUR1) between these neurons and pancreatic β-cells $K_{ATP}$ channels, lead to the further discovery that THB also block pancreatic β-cell $K_{ATP}$ channels, and can be developed to a novel anti-diabetic drugs.

Tetrahydroberberine (THB), isolated from the Chinese herb "*Corydalis ambigua*", exhibits a variety of pharmacological effects on the central nervous system (CNS). The l-tetrahydropalmatine (l-THP) and the l-stepholidine (l-SPD) are analogs of THB. Accumulating lines of evidence indicate that member of the terahydroprotoberberine (THPB) group of molecules exhibit the effects of sedation, hypnosis, antinociception, antischizophrenia, anti-hypertension, and the prevention of drug addiction. In addition, the morphological and biochemical experiments have demonstrated that THPBs also have neuroprotective effects. For instance, in transient ischemic rat models, SPD antagonized ischemic injury through eliminating the activation of calcium/calmodulin-dependent protein kinase II (CCDPKII), which has been reported to be involved in the mechanism of neuronal protection against ischemia. Furthermore, SPD also inhibited the release of lactate dehydrogenase (LDH), an indicator of injury, from neurons following ischemia, suggesting that SPD is able to decrease neuronal injury induced by hypoxia. Histological examination confirmed that SPD can protect striatal cells against transient cerebral ischemic injury and the neuroprotective effects of SPD may be related to its ability to scavenge hydroxyl free radicals.

Example 15

Figure 9:
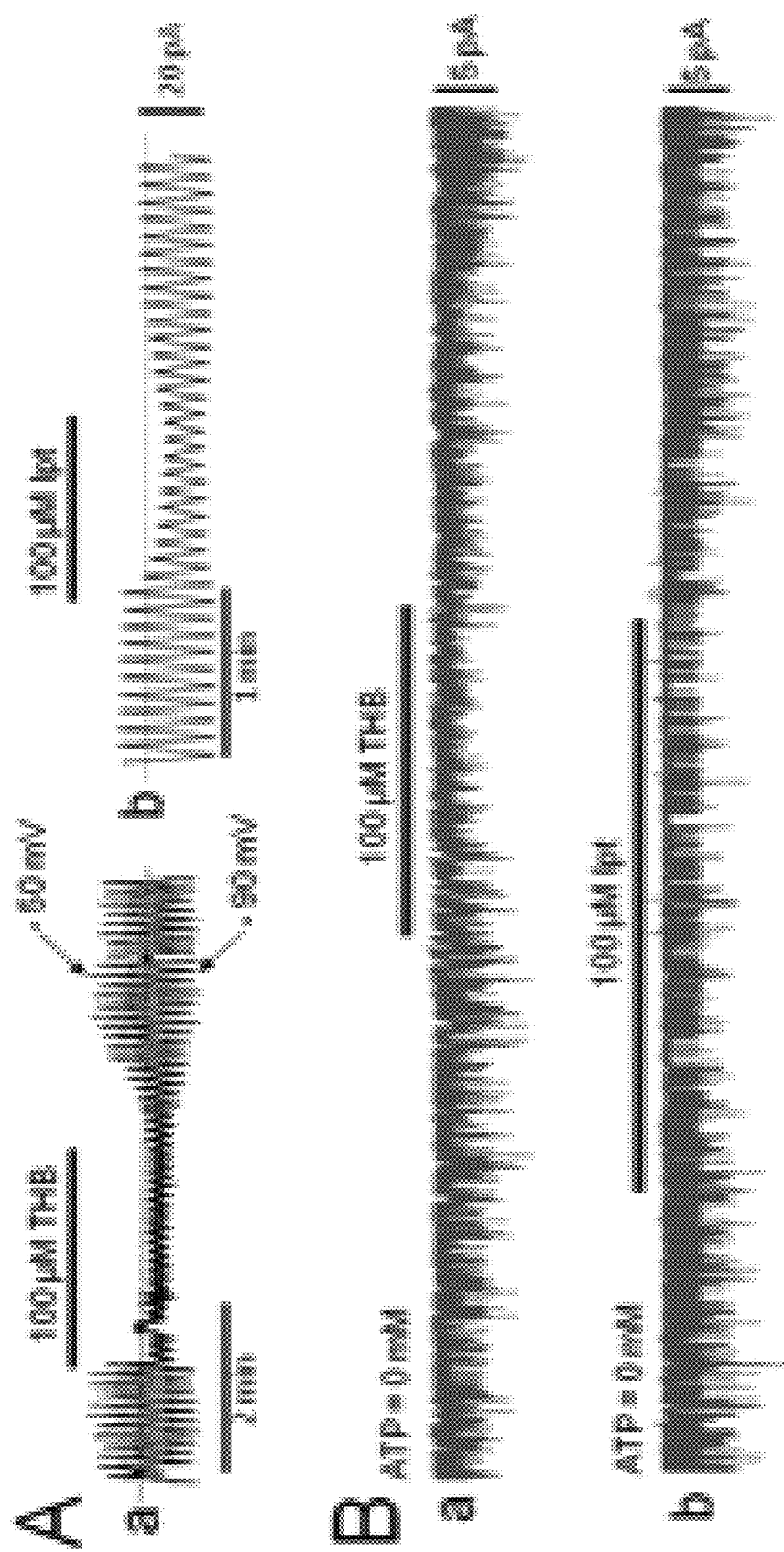
FIG. 9 depicts the effect of THB and Ipt on rat pancreatic β-cells. A: Bath application of either THB (100 μM) or Ipt (100 μM) reduced these β-cell $K_{ATP}$ channel-mediated currents. B: In inside-out patch recordings, bath-application of ATP free solution strongly opens $K_{ATP}$ channels, and under this condition, either THB or Ipt (bath-applied) inhibited these single channel activities.

THB and Ipt Reduced Both Whole-Cell and Single Channel Currents of $K_{ATP}$ Channels in Rat Pancreatic β-Cells To determine whether or not THB and Ipt can block pancreatic β-cell $K_{ATP}$ channels, whole-cell currents induced by repetitive ramp pulses from −90 to −50 mV (at 0.2 Hz) were recorded in voltage-clamp mode (external glucose=5.5 mM). Bath application of either THB (100 μM) or Ipt (100 μM) reduced these β-cell $K_{ATP}$ channel-mediated currents (FIG. 9, plot A). In inside-out patch recordings, bath-application of ATP free solution strongly opens $K_{ATP}$ channels, and under this condition, either THB or Ipt (bath-applied) inhibited these single channel activities (FIG. 9, plot B). These results indicate that both THB and Ipt are capable to inhibit pancreatic β-cell $K_{ATP}$ channels.

Example 16

Effects of THB and Ipt on Transfected Kir6.2SUR1 Channels in HEK-293 Cells

Figure 10:
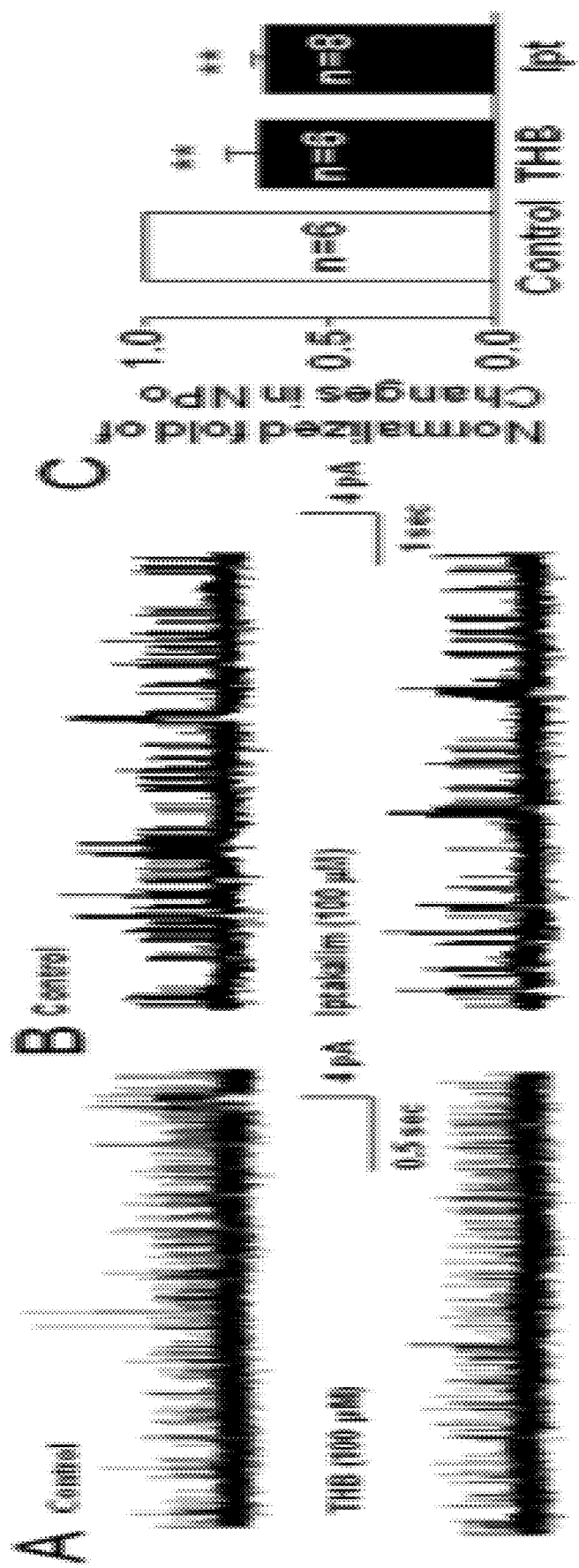
FIG. 10 depicts the effects of THB and Ipt on transfected Kir6.2SUR1 channels in HEK-293 cells. A: Patch-clamp cell attached recordings showed that THB (100 μM) reduced the single-channel currents of Kir6.2SUR1 $K_{ATP}$ channels. B: Patch-clamp cell attached recordings showed that Ipt (100 μM) reduced the single-channel currents of Kir6.2SUR1 $K_{ATP}$ channels. C: Normalized NPo values for THB was 0.51±0.05 (P<0.01; 6 patches), for Ipt was 0.50±0.02 (P<0.001; 8 patches), respectively.

To further determine the effects of THB and Ipt on pancreatic β-cell-type $K_{ATP}$ channels, the inventor examined the effects of THB or Ipt on the transfected Kir6.2SUR1 $K_{ATP}$ channels in HEK-293 cells. Patch-clamp cell attached recordings showed that either THB (100 μM) or Ipt (100 μM) reduced the single-channel currents of Kir6.2SUR1 $K_{ATP}$ channels (FIG. 10, plots A-C), and the normalized NPo value for THB was 0.51±0.05 (P<0.01; 6 patches), for Ipt was 0.50±0.02 (P<0.001; 8 patches), respectively (FIG. 10, plot C; control as 1; two-tailed, one-sample t test). These results further support our findings in rat β-cells that both THB and Ipt suppress the function of β-cell $K_{ATP}$ channels.

Example 17

Effects of Ipt on Different Subtypes of $K_{ATP}$ Channels

Figure 11:
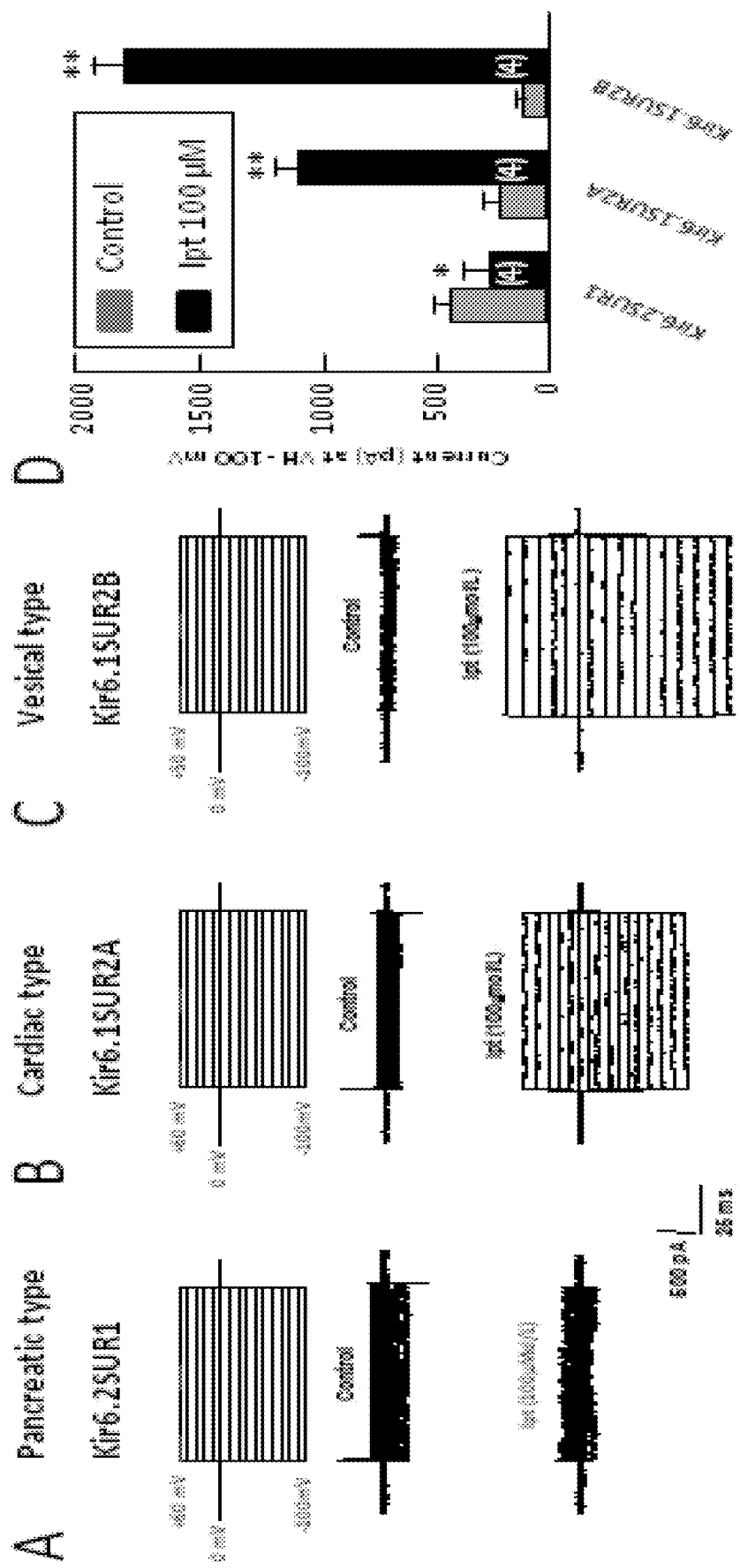
FIG. 11 depicts the effects of Ipt on different subtypes of $K_{ATP}$ channels. Using whole-cell recordings in voltage-clamp mode, Command pulse protocol was set by the series test pulses with 100 ms duration that were applied between −100 and +50 mV in 10 mV steps from a holding potential of 0 mV from different $K_{ATP}$ channels (A pancreatic type) (B cardiac type) and (C vesicle type). Representative effects of Ipt (100 μM perfused for 30 sec) on whole-cell current traces recorded from a cell expressed Kir6.2/SUR1 (A), Kir6.2/SUR2A (B) or Kir6.1/SUR2B (C). D summarizes data for currents measured at −100 mV from A-C. Values are means±S.E.M. (n=4). *P<0.05, **P<0.01 vs. control.

Using whole-cell recordings in voltage-clamp mode, Command pulse protocol was set by the series test pulses with 100 ms duration that were applied between −100 and +50 mV in 10 mV steps from a holding potential of 0 mV (Top traces in FIG. 11, plots A-C). Representative effects of Ipt (100 μM perfused for 30 sec) on whole-cell current traces recorded from a cell expressed Kir6.2/SUR1 (A), Kir6.2/SUR2A (B) or Kir6.1/SUR2B (C). FIG. 11, plot D summarizes data for currents measured at −100 mV from A-C. Values are means±S.E.M. (n=4). *P<0.05, **P<0.01 vs. control. These results suggest that Ipt exhibits bi-directive modulation of $K_{ATP}$ channels and blocks β-cell-type $K_{ATP}$ channels while opens cardiovascular types of $K_{ATP}$ channels.

Example 18

THB and Ipt Increased Insulin Release from Rat Pancreatic Islets

Figure 12:
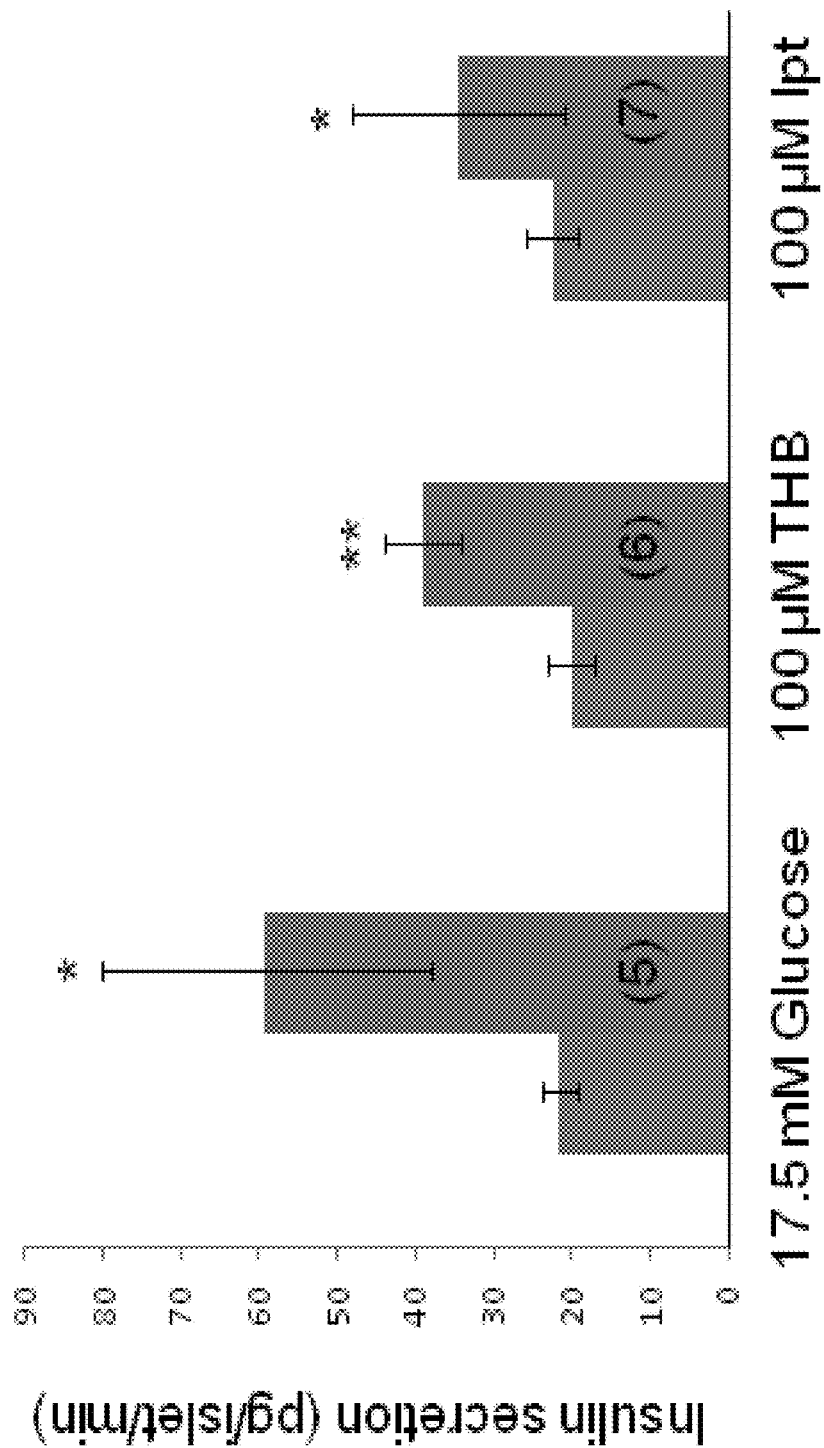
FIG. 12 depicts that administration of THB and Ipt increase insulin release from pancreatic islets. The application of 17.5 mM glucose increased insulin secretion from a basal level of 21.5±0.9 to 59.2±8.6 pg/islet/min (P<0.01; 5 cells). Bath application of 100 THB increased insulin secretion from 22.5±1.2 to 39.4±1.5 pg/islet/min (P<0.01; 6 cells) and 100 μM Ipt increased insulin secretion from 22.5±1.2 to 34.5±1.8 pg/islet/min.

With 5.5 mM glucose in the external solution, basal insulin secretion was measured. As shown in FIG. 12, the application of 17.5 mM glucose increased insulin secretion from a basal level of 21.5±0.9 to 59.2±8.6 pg/islet/min (P<0.01; 5 cells). Bath application of 100 μM THB increased insulin secretion from 22.5±1.2 to 39.4±1.5 pg/islet/min (FIG. 5; P<0.01; 6 cells) and 100 μM Ipt increased insulin secretion from 22.5±1.2 to 34.5±1.8 pg/islet/min (FIG. 11; P<0.05; 7 cells). These data demonstrate that both THB and Ipt increase insulin secretion, presumably by closing $K_{ATP}$ channels in rat pancreatic β-cells.

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as may be taught or suggested herein. A variety of advantageous and disadvantageous alternatives are mentioned herein. It is to be understood that some preferred embodiments specifically include one, another, or several advantageous features, while others specifically exclude one, another, or several disadvantageous features, while still others specifically mitigate a present disadvantageous feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be mixed and matched by one of ordinary skill in this art to perform methods in accordance with principles described herein. Among the various elements, features, and steps some will be specifically included and others specifically excluded in diverse embodiments.

Although the invention has been disclosed in the context of certain embodiments and examples, it will be understood by those skilled in the art that the embodiments of the invention extend beyond the specifically disclosed embodiments to other alternative embodiments and/or uses and modifications and equivalents thereof.

Many variations and alternative elements have been disclosed in embodiments of the present invention. Still further variations and alternate elements will be apparent to one of skill in the art. Among these variations, without limitation, are the sources of Ipt, THB, pharmaceutical compositions containing THB and Ipt, methods of manufacturing and administering such pharmaceutical compositions, therapeutic approaches using THB and the particular use of the products created through the teachings of the invention. Various embodiments of the invention can specifically include or exclude any of these variations or elements.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Variations on those preferred embodiments will become apparent to those of ordinary skill in the art upon reading the foregoing description. It is contemplated that skilled artisans can employ such variations as appropriate, and the invention can be practiced otherwise than specifically described herein. Accordingly, many embodiments of this invention include all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

In closing, it is to be understood that the embodiments of the invention disclosed herein are illustrative of the principles of the present invention. Other modifications that can be employed can be within the scope of the invention. Thus, by way of example, but not of limitation, alternative configurations of the present invention can be utilized in accordance with the teachings herein. Accordingly, embodiments of the present invention are not limited to that precisely as shown and described.

REFERENCES

[1] C. F. Bian, S. M. Duan, S. H. Xing, Y. M. Yu, W. Qin, G. Z. Jin, Y. Chen, [Interaction of analgesics and l-stepholidine], Zhongguo Yao Li Xue Bao 7 (1986) 410-413.
[2] L. F. Chen, J. Z. Gao, F. C. Wang, [Analgesic and antipyretic effects of lstepholidine without addiction], Zhongguo Yao Li Xue Bao 7 (1986) 311-314.
[3] L. F. Chen, J. Z. Gao, F. C. Wang, C. R. Yang, [Analgesic, sedative and antispastic effects of l-stepholidine], Zhongguo Yao Li Xue Bao 6 (1985) 156-158.
[4] H. Chu, G. Jin, E. Friedman, X. Zhen, Recent development in studies of tetrahydroprotoberberines: mechanism in antinociception and drug addiction, Cell Mol Neurobiol 28 (2008) 491-499.
[5] Y. Fu, Z. T. Zhu, X. Z. Zhu, G. Z. Jin, Biphasic firing response of nucleus accumbens neurons elicited by THPB-18 and its correlation with DA receptor subtypes, Acta Pharmacol Sin 25 (2004) 1597-1605.
[6] M. Giustizieri, M. L. Cucchiaroni, E. Guatteo, G. Bernardi, N. B. Mercuri, N. Berretta, Memantine inhibits ATP-dependent K+ conductances in dopamine neurons of the rat substantia nigra pars compacta, J Pharmacol Exp Ther 322 (2007) 721-729.
[7] G. Hu, Y. Hu, G. Z. Jin, Antagonism of l-stepholidine on D2 receptor-mediated inhibition of synaptosomal adenylate cyclase in rat corpus striatum, Zhongguo Yao Li Xue Bao 13 (1992) 104-110.
[8] K. Ishihara, M. Alkondon, J. G. Montes, E. X. Albuquerque, Nicotinic responses in acutely dissociated rat hippocampal neurons and the selective blockade of fast-desensitizing nicotinic currents by lead, J Pharmacol Exp Ther 273 (1995) 1471-1482.
[9] G. Z. Jin, K. X. Huang, B. C. Sun, Dual actions of (−)-stepholidine on dopamine receptor subtypes after substantia nigra lesion, Neurochem Int 20 Suppl (1992) 175S-178S.

[10] G. Z. Jin, Z. T. Zhu, Y. Fu, (−)-Stepholidine: a potential novel antipsychotic drug with dual D1 receptor agonist and D2 receptor antagonist actions, Trends Pharmacol Sci 23 (2002) 4-7.

[11] X. L. Jin, Y. Shao, M. J. Wang, L. J. Chen, G. Z. Jin, Tetrahydroprotoberberines inhibit lipid peroxidation and scavenge hydroxyl free radicals, Acta Pharmacol Sin 21 (2000) 477-480.

[12] M. G. Lacey, N. B. Mercuri, R. A. North, Two cell types in rat substantia nigra zona compacta distinguished by membrane properties and the actions of dopamine and opioids, J Neurosci 9 (1989) 1233-1241.

[13] P. K. Li, L. J. Chen, H. Zhao, G. Z. Jin, Treatment of Parkinson disease with lstepholidine (SPD) plus bromocriptine, Chin J Integrated Tradit West Med 19 (1999) 428-429.

[14] X. T. Li, Y. L. Wang, J. X. Wang, S. J. Yang, [Effects of tetrahydroprotoberberines on cytosolic free calcium in cultured rat single myocardial cells], Yao Xue Xue Bao 30 (1995) 567-572.

[15] B. Liss, O. Haeckel, J. Wildmann, T. Miki, S. Seino, J. Roeper, K-ATP channels promote the differential degeneration of dopaminergic midbrain neurons, Nat Neurosci 8 (2005) 1742-1751.

[16] G. Q. Liu, B. Y. Han, E. H. Wang, [Blocking actions of l-stephanine, xylopine and 7 other tetrahydroisoquinoline alkaloids on alpha adrenoceptors], Zhongguo Yao Li Xue Bao 10 (1989) 302-306.

[17] Y. S. Miao, A. Z. Zhang, C. Lin, M. H. Jiang, G. Z. Jin, [Effects of l-stepholidine on isolated rabbit basilar artery, mesenteric artery, and thoracic aorta], Zhongguo Yao Li Xue Bao 12 (1991) 260-262.

[18] C. Neusch, D. Runde, A. Moser, G proteins modulate D2 receptor-coupled K(ATP) channels in rat dopaminergic terminals, Neurochem Res 25 (2000) 1521-1526.

[19] G. Paxinos, C. Watson, The rat brain in stereotaxic coordinates, Academic Press, San Diego, Calif., 1998.

[20] B. Salthun-Lassalle, E. C. Hirsch, J. Wolfart, M. Ruberg, P. P. Michel, Rescue of mesencephalic dopaminergic neurons in culture by low-level stimulation of voltage-gated sodium channels, J Neurosci 24 (2004) 5922-5930.

[21] D. L. Shen, G. Z. Jin, Y. F. He, Z. D. Zhang, Z. Sun, Y. Q. Lu, Z. C. Yang, [Effect of (−)-stepholidine on blood pressure and alpha-adrenoceptor agonists-, KCl- and CaCl2-evoked contractions of aortic strips], Zhongguo Yao Li Xue Bao 12 (1991) 514-518.

[22] W. X. Shi, Y. Chen, G. Z. Jin, [Effect of l-stepholidine on rotational behavior in rats], Zhongguo Yao Li Xue Bao 5 (1984) 222-225.

[23] B. C. Sun, G. Z. Jin, Characteristics of (−)-stepholidine on the firing activity of substantia nigral dopamine neurons after repeated reserpine treatment, Biol Signals 1 (1992) 331-338.

[24] X. D. Sun, E. W. Lee, E. H. Wong, K. S. Lee, ATP-sensitive potassium channels in freshly dissociated adult rat striatal neurons: activation by metabolic inhibitors and the dopaminergic receptor agonist quinpirole, Pflugers Arch 440 (2000) 530-547.

[25] F. M. Tang, Y. M. Ding, Y. T. Chen, Y. F. Sun, R. Wang, G. Y. Zhang, G. Z. Jin, Antagonistic effect of l-stepholidine on striatal ischemic injury in rat, Zhongguo Yao Li Xue Bao 20 (1999) 1073-1078.

[26] H. Uno, H. Kobayashi, Y. Handa, M. Kabuto, T. Kubota, Alterations of calcium/calmodulin-dependent protein kinase II activity in ischaemia-induced neuronal death and neuronal protection against ischaemia in the gerbil hippocampus, Acta Neurochir (Wien) 141 (1999) 287-294.

[27] J. Wu, P. X. Chen, G. Z. Jin, Dopamine-induced ionic currents in acutely dissociated rat neurons of CNS, Zhongguo Yao Li Xue Bao 17 (1996) 23-27.

[28] J. Wu, A. A. George, K. M. Schroeder, L. Xu, S. Marxer-Miller, L. Lucero, R. J. Lukas, Electrophysiological, pharmacological, and molecular evidence for alpha7-nicotinic acetylcholine receptors in rat midbrain dopamine neurons, J Pharmacol Exp Ther 311 (2004) 80-91.

[29] J. Wu, J. Hu, Y. P. Chen, T. Takeo, S. Suga, J. Dechon, Q. Liu, K. C. Yang, P. A. St John, G. Hu, H. Wang, M. Wakui, Iptakalim modulates ATP-sensitive K(+) channels in dopamine neurons from rat substantia nigra pars compacta, J Pharmacol Exp Ther 319 (2006) 155-164.

[30] J. Wu, G. Z. Jin, Tetrahydroberberine blocks membrane K+ channels underlying its inhibition of intracellular message-mediated outward currents in acutely dissociated CA1 neurons from rat hippocampus, Brain Res 775 (1997) 214-218.

[31] J. Wu, G. Z. Jin, Tetrahydroberberine inhibits acetylcholine-induced K+ current in acutely dissociated rat hippocampal CA1 pyramidal neurons, Neurosci Lett 222 (1997) 115-118.

[32] J. Wu, G. Z. Jin, Tetrahydroberberine suppresses dopamine-induced potassium current in acutely dissociated CA1 pyramidal neurons from rat hippocampus, Neurosci Lett 207 (1996) 155-158.

[33] Z. L. Xiong, Z. Sun, G. Z. Jin, Y. Chen, [Influence of l-stepholidine on blood pressure and its relation to alpha-adrenoceptors], Zhongguo Yao Li Xue Bao 8 (1987) 497-501.

[34] K. Yang, J. Hu, L. Lucero, Q. Liu, C. Zheng, X. Zhen, G. Jin, R. J. Lukas, J. Wu, Distinctive nicotinic acetylcholine receptor functional phenotypes of rat ventral tegmental area dopaminergic neurons, J Physiol 587 (2009) 345-361.

[35] K. Yang, G. Jin, J. Wu, The neuropharmacology of (−)-stepholidine and its potential applications, Curr Neuropharmacol 5 (2007) 289-294.

[36] L. Zhang, R. Zhou, G. Xiang, Stepholidine protects against H2O2 neurotoxicity in rat cortical neurons by activation of Akt, Neurosci Lett 383 (2005) 328-332.

[37] X. X. Zhang, J. Liu, Y. Fu, G. Y. Hu, G. Z. Jin, Action sites of rotation and unit firing induced by l-stepholidine and DA agonists in basal ganglia of 6-OHDAlesioned rats, Zhongguo Yao Li Xue Bao 20 (1999) 979-986.

[38] X. X. Zhang, Z. T. Zhu, G. Z. Jin, Comparison of (−)-stepholidine and D1 or D2 agonists on unit firing of globus pallidus in 6-hydroxydopamine-lesioned rats, Life Sci 63 (1998) 537-544.

[39] Z. D. Zhang, G. Z. Jin, S. X. Xu, L. P. Yu, Y. Chen, F. Y. Jiang, Y. R. Zhang, Z. Sun, Y. L. Ding, C. F. Bian, et al., [Effects of l-stepholidine on the central nervous and cardiovascular systems], Zhongguo Yao Li Xue Bao 7 (1986) 522-526.

[40] Z. T. Zhu, Y. Fu, G. Y. Hu, G. Z. Jin, Electrophysiological study on biphasic firing activity elicited by D(1) agonistic-D(2) antagonistic action of (−)-stepholidine in nucleus accumbens, Sheng Li Xue Bao 52 (2000) 123-130.

The invention claimed is:
1. A method of treating diabetes in a subject with diabetes, the method comprising the steps of:

providing a quantity of a composition comprising tetrahydroberberine (THB) and Iptakalim (Ipt) or salts thereof; and treating the subject by administering a therapeutically effective amount of the composition.

2. The method of claim 1, wherein administering the composition effectively inhibits $K_{ATP}$ channel signaling in the subject's pancreas.

3. The method of claim 2, wherein the $K_{ATP}$ channel is Kir6.2/SUR1 subtype.

4. The method of claim 1, wherein administering the composition does not inhibit $K_{ATP}$ channel signaling in the subject's cardiovascular system.

5. The method of claim 4, wherein the $K_{ATP}$ channel is Kir6.2/SUR2A or KIR6.2/SUR2B subtypes.

6. The method of claim 1, wherein the subject is a human.

7. The method of claim 1, wherein the composition is administered intravenously, orally, topically, and/or through direct injection.

8. A method of selectively inhibiting $K_{ATP}$ channel signaling in pancreatic β-cells to treat diabetes in a subject, the method comprising the steps of:

providing a quantity of a composition comprising tetrahydroberberine (THB) and Iptakalim (Ipt), or salts thereof; and treating the subject by administering a therapeutically effective amount of the composition.

9. The method of claim 8, wherein administering the composition does not inhibit $K_{ATP}$ channel signaling in the subject's cardiovascular tissue or smooth muscle tissue.

10. The method of claim 9, wherein the pancreatic β-cell $K_{ATP}$ channel is Kir6.2/SUR1 subtype, the cardiovascular tissue $K_{ATP}$ channel is Kir6.2/SUR2A subtype, and the smooth muscle tissue is Kir6.2/SUR2B subtype.

11. The method of claim 8, wherein the composition comprises a third active ingredient.

12. A method of treating diabetes in a subject without inhibiting $K_{ATP}$ channel signaling in the subject's cardiovascular tissue, the method comprising the steps of:

providing a quantity of a composition comprising tetrahydroberberine (THB) and Iptakalim (Ipt), or salts thereof; and treating the subject by administering a therapeutically effective amount of the composition, wherein administration the composition does not inhibit $K_{ATP}$ channel signaling in the subject's cardiovascular tissue.

13. The method of claim 12, wherein administration of the composition effectively inhibits $K_{ATP}$ channel signaling in the subject's pancreas, wherein pancreas $K_{ATP}$ channel is Kir6.2/SUR1 subtype.

14. The method of claim 12 wherein the $K_{ATP}$ channel of the subject's cardiovascular tissue is Kir6.2/SUR2A subtype.

* * * * *